US012735499B2

(12) United States Patent
Cox et al.

(10) Patent No.: US 12,735,499 B2
(45) Date of Patent: Sep. 15, 2026

(54) IMMUNOGLOBULIN SINGLE DOMAIN ANTIBODIES FOR DELIVERY OF MUCOSAL VACCINES

(71) Applicants: Universiteit Gent, Ghent (BE); VIB VZW, Zwijnaarde (BE)

(72) Inventors: Eric Cox, Oosterzele (BE); Bert Devriendt, Mariakerke (BE); Anna Depicker, Schelderode (BE)

(73) Assignees: UNIVERSITEIT GENT, Ghent (BE); VIB VZW, Zwijnaarde (BE)

( * ) Notice: Subject to any disclaimer, the term of this patent is extended or adjusted under 35 U.S.C. 154(b) by 1092 days.

(21) Appl. No.: 17/793,217

(22) PCT Filed: Jan. 15, 2021

(86) PCT No.: PCT/EP2021/050798

§ 371 (c)(1),
(2) Date: Jul. 15, 2022

(87) PCT Pub. No.: WO2021/144415

PCT Pub. Date: Jul. 22, 2021

(65) Prior Publication Data

US 2023/0076670 A1 Mar. 9, 2023

(30) Foreign Application Priority Data

Jan. 17, 2020 (EP) .................................... 20152428

(51) Int. Cl.

*C07K 16/28* (2006.01)
*A61K 39/00* (2006.01)
*A61K 39/395* (2006.01)
*A61P 1/00* (2006.01)
*C12N 15/81* (2006.01)

(52) U.S. Cl.

CPC .... *C07K 16/2896* (2013.01); *A61K 39/39533* (2013.01); *A61P 1/00* (2018.01); *C12N 15/81* (2013.01); *A61K 2039/505* (2013.01); *C07K 2317/52* (2013.01); *C07K 2317/565* (2013.01)

(58) Field of Classification Search

CPC .......... C07K 16/2896; C07K 2317/569; C07K 2319/33

See application file for complete search history.

(56) References Cited

FOREIGN PATENT DOCUMENTS

WO PCT/WO2009/103555 A2 8/2009
WO PCT/WO2009/103555 A3 8/2009
WO WO-2019210155 A1 * 10/2019 ......... A61K 47/6849

OTHER PUBLICATIONS

Mitchell, Laura S., and Lucy J. Colwell. "Analysis of nanobody paratopes reveals greater diversity than classical antibodies." Protein Engineering, Design and Selection 31.7-8 (2018): 267-275. (Year: 2018).*

Chiu, Mark L., et al. "Antibody structure and function: the basis for engineering therapeutics." Antibodies 8.4 (2019): 55. (Year: 2019).*

Edwards, Bryan M., et al. "The remarkable flexibility of the human antibody repertoire; isolation of over one thousand different antibodies to a single protein, BLyS." Journal of molecular biology 334.1 (2003): 103-118. (Year: 2003).*

Rudikoff, Stuart, et al. "Single amino acid substitution altering antigen-binding specificity." Proceedings of the National Academy of Sciences 79.6 (1982): 1979-1983. (Year: 1982).*

Brown, McKay, et al. "Tolerance of single, but not multiple, amino acid replacements in antibody VH CDR 2: a means of minimizing B cell wastage from somatic hypermutation?." The Journal of Immunology 156.9 (1996): 3285-3291. (Year: 1996).*

Baert, et al., "β-glucan microparticles targeted to epithelial APN as oral antigen delivery system" Oct. 17, 2015, Elsevier B.V., Belgium.

Shruti, et al., "A two-amino acid mutation in murine IgA enables downstream processing and purification on staphylococcal superantigen-like protein 7" Feb. 13, 2019, Elsevier B.V., Belgium.

Cheng, et al., "The use of single chain Fv as targeting agents for immunoliposomes: an update on immunoliposomal drugs for cancer treatment" Expert Opin Drug Deliv. Apr. 2010 ; 7(4): 461-478. Canada.

Coddens, "Cranberry extract inhibits in vitro adhesion of F4 and F18+ *Escherichia coli* to pig intestinal epithelium and reduces in vivo excretion of pigs orally challenged with F18+ verotoxigenic *E. coli*" Veterinary Microbiology 202 (2017) 64-71. Belgium.

Xiao-Chi, et al., "A novel method of Multiplexed Competitive Antibody Binning for the characterization of monoclonal antibodies." Journal of immunological methods vol. 288,1-2 (2004): 91-8. USA.

Bakshi, et al., "A two-amino acid mutation in murine IgA enables downstream processing and purification on staphylococcal superantigen-like protein 7" Feb. 13, 2019, Elsevier B.V., Belgium.

International Search Report & Written Opinion in reference to co-pending PCT International Patent Application No. PCT/EP2021/050798.

Conrath, et al., "-Lactamase Inhibitors Derived from Single-Domain Antibody Fragments Elicited in the Camelidae" Antimicrob Agents Chemother. Oct. 2001, 45(10):2807-12. UAE.

(Continued)

*Primary Examiner* — Julie Wu
*Assistant Examiner* — Bryan William Heck
(74) *Attorney, Agent, or Firm* — DINSMORE & SHOHL LLP

(57) ABSTRACT

The present invention relates to single-domain antibodies that specifically bind aminopeptidase N (APN), and more in particular to polypeptides, and nucleic acids encoding such polypeptides; to methods for preparing such polypeptides; to compositions and in particular to pharmaceutical compositions that comprise such polypeptides, for prophylactic, therapeutic or diagnostic purposes. In particular, the single-domain antibodies of the present invention are capable of targeting a moiety to a mucosal surface.

16 Claims, 12 Drawing Sheets

Specification includes a Sequence Listing.

(56) References Cited

OTHER PUBLICATIONS

Davies, et al., Single antibody domains as small recognition units: design and in vitro antigen selection of camelized, human VH domains with improved protein stability. Protein engineering, 9(6), 531-537. USA.
De Genst, et al. "Chemical basis for the affinity maturation of a camel single domain antibody." Department of Molecular and Cellular Interactions, The Journal of biological chemistry, vol. 279, 51, 2004 Belgium.
De Meyer, et al. "Nanobody-based products as research and diagnostic tools." Trends in biotechnology vol. 32,5 (2014): 263-70. Belgium.
De Meyer [2] "Comparison of VHH-Fc antibody production in *Arabidopsis thaliana*, Nicotiana benthamiana and Pichia pastoris" Plant Biotechnology Journal (2015), pp. 938-947. Belgium.
Devriendt, et al. "The food contaminant fumonisin B1 reduces the maturation of porcine CD11R1+ intestinal antigen presenting cells and antigen-specific immune responses, leading to a prolonged intestinal ETEC infection." Veterinary research vol. 40,4 (2009): 40. Belgium.
Devriendt, et al. "Crossing the barrier: Targeting epithelial receptors for enhanced oral vaccine delivery." Journal of controlled release : official journal of the Controlled Release Society vol. 160,3 (2012): 431-9. Belgium.
Drake et al. "Characterizing high-affinity antigen/antibody complexes by kinetic- and equilibrium-based methods." Analytical biochemistry vol. 328,1 (2004): 35-43. USA.
Duarte, et al. "Characterizing high-affinity antigen/antibody complexes by kinetic- and equilibrium-based methods" Anal Biochem. May 1, 2004;328(1):35-43. USA.
Fontijn "CD13/Aminopeptidase N overexpression by basic fibroblast growth factor mediates enhanced invasiveness of 1F6 human melanoma cells." British journal of cancer vol. 94,11 (2006): 1627-36. Netherlands.
Fraley, et al., "The Gyrolab™ immunoassay system: a platform for automated bioanalysis and rapid sample turnaround" Bioanalysis, vol. 5, Issue 14. 2013. 1765-1774. USA.
Helma, et al., "Nanobodies and recombinant binders in cell biology." The Journal of cell biology vol. 209,5 (2015): 633-44. Germany.
Imamura, et al., "Effect of ubenimex (Bestatin) on the cell growth and phenotype of HL-60 and HL-60R cell lines: up- and down-regulation of CD13/aminopeptidase N. Leuk Lymphoma." Leukemia & lymphoma vol. 37,5-6 (2000): 663-7. Japan.
International Search Report mailed Apr. 22, 2021, in International Application No. PCT/2021/050798.
Kurtzman "Biotechnological strains of Komagataella (Pichia) pastoris are Komagataella phaffii as determined from multigene sequence analysis." Journal of industrial microbiology & biotechnology, 36(11), 1435-1438. USA.
Lundqvist, et al., "Isolation of functionally active intraepithelial lymphocytes and enterocytes from human small and large intestine." Journal of immunological methods vol. 152,2 (1992): 253-63. Sweden.
Melkebeek, et al., "Targeting aminopeptidase N , a newly identified receptor for F4ac fimbriae, enhances the Intestinal mucosal immune response" Mucosal immunology, 5(6), 635-645. 2012. Belgium.
Miller, et al., "Epitope binning of murine monoclonal antibodies by a multiplexed pairing assay" Journal of immunological methods, Feb. 28, 2011;365(1-2):118-25. Epub Jan. 9, 2011. USA.
Moonens, et al., "Nanobody mediated inhibition of attachment of F18 Fimbriae expressing *Escherichia coli*" PloS one, 9(12). Belgium.
Muyldermans, et al., "Nanobodies: Natural Single-Domain Antibodies" Annual review of biochemistry vol. 82 (2013): 775-97. Belgium.
Narasimham, et al., "Rational Design of Targeted Next-Generation Carriers for Drug and Vaccine Delivery." Annual review of biomedical engineering vol. 18 (2016): 25-49. USA.
Ober, et al., "Rational Design of Targeted Next-Generation Carriers for Drug and Vaccine Delivery." Annual review of biomedical engineering vol. 18 (2016): 25-49. USA.
Bakshi (eESR) "Evaluating single-domain antibodies as carriers for targeted vaccine delivery to the small intestinal epithelium" Journal of controlled release : official journal of the Controlled Release Society vol. 321 (2020). Belgium.
PCT/WO2019/191519 A1 filed Mar. 28, 2019 in the name of Orionis Biosciences, Inc.
Grieger, et al. (eESR) "Efficient targeting of CD13 on cancer cells by the immunotoxin scFv13-ETA' and the bispecific scFv [13xds16]." Journal of cancer research and clinical oncology vol. 143,11 (2017): 2159-2170. Germany.
Curnis, et al., (eESR) "Enhancement of tumor necrosis factor alpha antitumor immunotherapeutic properties by targeted delivery to aminopeptidase N (CD13)." Nature biotechnology vol. 18,11 (2000): 1185-90. Italy.
Baert, et al., (eESR) ""β-glucan microparticles targeted to epithelial APN as oral antigen delivery system." Journal of controlled release : official journal of the Controlled Release Society vol. 220,Pt A (2015): 149-159." Belgium.
Melkebeek, et al., (eESR) "Targeting aminopeptidase N, a newly identified receptor for F4ac fimbriae, enhances the intestinal mucosal immune response." Mucosal immunology vol. 5,6 (2012): 635-45. Belgium.
Pardon, et al., "A general protocol for the generation of Nanobodies for structural biology." Nature protocols vol. 9,3 (2014): 674-93. Belgium.
Robinson, et al., "Optimizing the stability of single-chain proteins by linker length and composition mutagenesis." Proceedings of the National Academy of Sciences of the United States of America vol. 95,11 (1998): 5929-34. USA.
Snoeck, et al., "Transcytosis of F4 fimbriae by villous and dome epithelia in F4-receptor positive pigs supports importance of receptor-dependent endocytosis in oral immunization strategies." Veterinary immunology and Immunopathology vol. 124,1-2 (2008): 29-40. Belgium.
Virdi, et al., "Orally fed seeds producing designer IgAs protect weaned piglets against enterotoxigenic *Escherichia coli* infection." Proceedings of the National Academy of Sciences of the United States of America vol. 110,29 (2013): 11809-14. Belgium.

* cited by examiner

FIG. 4
MFI (APN/parent)
1500
300
200
100
0
-100
2L65
3L2
3L73
2L42
2L52
2L76
3L26
2L63
2L69
2L22
3L22
2L34
3L17
3L85
3L94
2L48
2L81
3L12
3L84
3L11
2L2
2L18
2L60
3L1
2L46
2L58
2L8
3L72
IMMO13
BCII10
1
2
3
5
6
7
8
9
10
11
12
13
14

| Fam | Clone | Seq Id No | Amino acid sequence |
|---|---|---|---|
| 1 | 2L65 | 6 | QVQLQESGGGLVQPGGSLRLSCAGSGRTISNHAMGWFRQAPGKEREFVAAISWTGLTTNYADSVKGRFFISRDDAENTVYLQMNSLKPEDTAVYYCAARQSGYVSKFVDDYGYWGQGTQVTVSS |
|  | 3L2 | 7 | QVQLQESGGGLVQAGDSLRLSCAGSGRTISNHAMGWFRQAPGKEREFVAAISWTGLTTNYADSVKGRFFISRDDAENTVYLQMNSLEPEDTAVYYCAARQSGYVSKFVDDYGYWGQGTQVTVSS |
|  | 3L73 | 8 | QVQLQESGGGLVQAGGSLRLSCAASGRTFSSNAMGWFRQAPGKEREFVAAISWTGLTTNYADSVKGRFFISRDDAKNTVYLQMNSLKPEDTAVYYCAARQSGYASKFLDEYGYWGQGTQVTVSS |
| 8 | 3L94 | 9 | QVQLQESGGGLVQPGDSLRLSCAASGRTFSTYAMGWFRQAPGKEREFVAYISQLSLSTKYADSVKGRFTVSRDDAQNTLYLQMNSLRPEDTAVYYCATRSQNYVTTYDQSRAYDYWGQGTQVTVSS |

| Fam | Clone | Seq Id No | nucleic acid sequence |
|---|---|---|---|
| 1 | 2L65 | 10 | CAGGTGCAGCTGCAGGAGTCTGGGGGAGGCTTGGTGCAGCCTGGGGGGTCTCTGAGACTCTCCTGTGCAGGCTCTGGACGCACTATTAGCAACCATGCCATGGGCTGGTTCCGCCAGGCTCCAGGGAAGGAGCGCGAGTTTGTAGCAGCTATTAGCTGGACTGGACTTACCACGAACTATGCAGACTCCGTGAAGGGCCGATTCTTCATCTCCAGAGACGACGCCGAGAACACGGTGTATCTGCAAATGAACAGCCTGAAACCTGAAGACACGGCCGTTTATTACTGTGCAGCCCGCCAGTCCGGTTACGTGTCGAAATTCGTCGATGACTATGGCTACTGGGGCCAGGGGACCCAGGTCACCGTCTCCTCAGCGGCCGCATACCCGTACGACGTTCCGGACTACGGTTCCCACCACCATCACCATCACTAG |
|  | 3L2 | 11 | CAGGTGCAGCTGCAGGAGTCTGGGGGAGGATTGGTGCAGGCTGGGGACTCTCTGAGACTCTCCTGTGCAGGCTCTGGACGCACTATTAGCAACCATGCCATGGGCTGGTTCCGCCAGGCTCCAGGGAAGGAGCGCGAGTTTGTAGCAGCTATTAGCTGGACTGGACTTACCACGAACTATGCAGACTCCGTGAAGGGCCGATTCTTCATCTCCAGAGACGACGCCGAGAACACGGTGTATCTGCAAATGAACAGCCTGGAACCTGAAGACACGGCCGTTTATTACTGTGCAGCCCGCCAGTCCGGTTACGTGTCGAAATTCGTCGATGACTATGGCTACTGGGGCCAGGGGACCCAGGTCACCGTCTCCTCAGCGGCCGCATACCCGTACGACGTTCCGGACTACGGTTCCCACCACCATCACCATCACTAG |
|  | 3L73 | 12 | CAGGTGCAGCTGCAGGAGTCTGGGGGAGGATTGGTGCAGGCTGGGGGCTCTCTGAGACTCTCCTGCGCAGCCTCTGGACGCACCTTCAGTAGTAATGCCATGGGCTGGTTCCGCCAGGCTCCAGGGAAGGAGCGCGAGTTTGTAGCAGCTATTAGCTGGACTGGACTTACCACGAACTATGCAGACTCCGTGAAGGGCCGATTCTTCATCTCCAGAGACGACGCCAAGAACACGGTGTATCTGCAAATGAACAGCCTGAAACCTGAAGACACGGCCGTTTATTACTGTGCAGCCCGCCAGTCCGGTTACGCGTCGAAATTCCTCGATGAGTATGGCTACTGGGGCCAGGGGACCCAGGTCACCGTCTCCTCAGCGGCCGCATACCCGTACGACGTTCCGGACTACGGTTCCCACCACCATCACCATCACTAG |
| 8 | 3L94 | 13 | CAGGTGCAGCTGCAGGAGTCTGGGGGAGGATTGGTGTAGCCTGGGGACTCTCTGAGACTCTCCTGTGCAGCCTCTGGACGCACCTTCAGTACCTATGCCATGGGCTGGTTCCGCCAGGCTCCAGGGAAGGAGCGTGAGTTTGTAGCCTATATTAGTCAACTTAGTTTGAGCACAAAGTATGCAGACTCCGTGAAGGGCCGATTCACCGTCTCCAGAGACGACGCCCAGAACACGCTGTATCTGCAGATGAACAGTCTGAGACCTGAGGACACGGCCGTGTATTACTGTGCCACTAGGAGCCAAAATTATGTTACTACTTACGATCAGTCCAGGGCGTATGACTACTGGGGCCAGGGGACCCAGGTCACCGTCTCCTCAGCGGCCGCATACCCGTACGACGTTCCGGACTACGGTTCCCACCACCATCACCATCACTAG |

FIG. 8

QVQLQESGGGLVQPGGSLRLSCAGSGRTISNHAMGWFRQAPGKEREFVAAISWTGLTTNYADSVKGRF FISRDDAENTVYLQMNSLKPEDTAVYYCAARQSGYVSKFVDDYGYWGQGTQVTVSSEPRGPTIKPCPPCK CPAPNLLGGPSVFIFPPKIKDVLMISLSPIVTCVVVDVSEDDPDVQISWFVNNVEVHTAQTQTHREDYNSTLR VVSALPIQHQDWMSGKEFKCKVNNKDLPAPIERTISKPKGSVRAPQVYVLPPPEEEMTKKQVTLTCMVTDF MPEDIYVEWTNNGKTELNYKNTEPVLDSDGSYFMYSKLRVEKKNWVERNSYSCSVVHEGLHNHHTTKSFSR TPGK (SEQ ID NO: 17)

FIG. 9

VSETSPKIFPLTLGSSEPAGYVVIACLVRDFFPSEPLTVTWSPSREGVIVRNFPPAQAGGLYTMSSQLTL PVEQCPADQILKCQVQHLSKSSQSVNVPCKVLPSDPCPQCCKPSLSLQPPALADLLLGSNASLTCTLSGL KKSEGVSFTWQPSGGKDAVQASPTRDSCGCYSVSSILPGCADPWNKGETFSCTAAHSELKSALTATITKP KVNTFRPQVHLLPPPSEELALNELVTLTCLVRGFSPKDVLVRWLQGGQELPRDKYLVWESLPEPGQAIPT YAVTSVLRVDAEDWKQGDTFSCMVGHEALPLAFTQKTIDRLAGKPTHVNVSVVMAEAEGICY (SEQ ID NO: 18)

FIG. 10A

DPCPQCCKPSLSLQPPALADLLLGSNASLTCTLSGLKKSEGVSFTWQPSGGKDAVQASPTRDSCGCYSVSSILP GCADPWNKGETFSCTAAHSELKSALTATITKPKVNTFRPQVHLLPPPSEELALNELVTLTCLVRGFSPKDVLVR WLQGGQELPRDKYLVWESLPEPGQAIPTYAVTSVLRVDAEDWKQGDTFSCMVGHEALPLAFTQKTIDRLA GKPTHVNVSVVMAEAEGICY (SEQ ID NO: 19)

FIG. 10B

AYNTAPSVYPLAPCGRDVSDHNVALGCLVSSYFPEPVTVTWNSGALSRVVHTFPSVLQPSGLYSLSSMVI VAASSLSTLSYTCNVYHPATNTKVDKRVDIEPPTPICPEICSCPAAEVLGAPSVFLFPPKPKDILMISRT PKVTCVVVDVSQEEAEVQFSWYVDGVQLYTAQTRPMEEQFNSTYRVVSVLPIQHQDWLKGKEFKCKVNNK DLLSPITRTISKATGPSRVPQVYTLPPAWEELSKSKVSITCLVTGFYPPDIDVEWQSNGQQEPEGNYRTT PPQQDVDGTYFLYSKLAVDKVRWQRGDLFQCAVMHEALHNHYTQKSISKTQGK (SEQ ID NO: 20)

FIG. 10C

APSVYPLAPCGRDVSDHNVALGCLVSSYFPEPVTVTWNSGALSRVVHTFPSVLQPSGLYSLSSMVI VAASSLSTLSYTCNVYHPATNTKVDKRVDIEPPTPICPEICSCPAAEVLGAPSVFLFPPKPKDILMISRT PKVTCVVVDVSQEEAEVQFSWYVDGVQLYTAQTRPMEEQFNSTYRVVSVLPIQHQDWLKGKEFKCKVNNK DLLSPITRTISKATGPSRVPQVYTLPPAWEELSKSKVSITCLVTGFYPPDIDVEWQSNGQQEPEGNYRTT PPQQDVDGTYFLYSKLAVDKVRWQRGDLFQCAVMHEALHNHYTQKSISKTQGK (SEQ ID NO: 21)

FIG. 10D

SEQUENCE LISTING

```
<160> NUMBER OF SEQ ID NOS: 21

<210> SEQ ID NO 1
<211> LENGTH: 10
<212> TYPE: PRT
<213> ORGANISM: Artificial sequence
<220> FEATURE:
<223> OTHER INFORMATION: CDR sequence

<400> SEQUENCE: 1

Gly Arg Thr Ile Ser Asn His Ala Met Gly
1               5                   10


<210> SEQ ID NO 2
<211> LENGTH: 10
<212> TYPE: PRT
<213> ORGANISM: Artificial sequence
<220> FEATURE:
<223> OTHER INFORMATION: CDR sequence
```

<400> SEQUENCE: 2

```
Gly Arg Thr Phe Ser Ser Asn Ala Met Gly
1               5                   10
```

<210> SEQ ID NO 3
<211> LENGTH: 10
<212> TYPE: PRT
<213> ORGANISM: Artificial sequence
<220> FEATURE:
<223> OTHER INFORMATION: CDR sequence

<400> SEQUENCE: 3

```
Ala Ile Ser Trp Thr Gly Leu Thr Thr Asn
1               5                   10
```

<210> SEQ ID NO 4
<211> LENGTH: 15
<212> TYPE: PRT
<213> ORGANISM: Artificial sequence
<220> FEATURE:
<223> OTHER INFORMATION: CDR sequence

<400> SEQUENCE: 4

```
Arg Gln Ser Gly Tyr Val Ser Lys Phe Val Asp Asp Tyr Gly Tyr
1               5                   10                  15
```

<210> SEQ ID NO 5
<211> LENGTH: 15
<212> TYPE: PRT
<213> ORGANISM: Artificial sequence
<220> FEATURE:
<223> OTHER INFORMATION: CDR sequence

<400> SEQUENCE: 5

```
Arg Gln Ser Gly Tyr Ala Ser Lys Phe Leu Asp Glu Tyr Gly Tyr
1               5                   10                  15
```

<210> SEQ ID NO 6
<211> LENGTH: 124
<212> TYPE: PRT
<213> ORGANISM: Artificial sequence
<220> FEATURE:
<223> OTHER INFORMATION: Single domain antibody

<400> SEQUENCE: 6

```
Gln Val Gln Leu Gln Glu Ser Gly Gly Gly Leu Val Gln Pro Gly Gly
1               5                   10                  15

Ser Leu Arg Leu Ser Cys Ala Gly Ser Gly Arg Thr Ile Ser Asn His
            20                  25                  30

Ala Met Gly Trp Phe Arg Gln Ala Pro Gly Lys Glu Arg Glu Phe Val
        35                  40                  45

Ala Ala Ile Ser Trp Thr Gly Leu Thr Thr Asn Tyr Ala Asp Ser Val
    50                  55                  60

Lys Gly Arg Phe Phe Ile Ser Arg Asp Asp Ala Glu Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Gln Ser Gly Tyr Val Ser Lys Phe Val Asp Asp Tyr Gly
            100                 105                 110

Tyr Trp Gly Gln Gly Thr Gln Val Thr Val Ser Ser
        115                 120
```

<210> SEQ ID NO 7
<211> LENGTH: 124
<212> TYPE: PRT
<213> ORGANISM: Artificial sequence
<220> FEATURE:
<223> OTHER INFORMATION: Single domain antibody

<400> SEQUENCE: 7

```
Gln Val Gln Leu Gln Glu Ser Gly Gly Gly Leu Val Gln Ala Gly Asp
1               5                   10                  15

Ser Leu Arg Leu Ser Cys Ala Gly Ser Gly Arg Thr Ile Ser Asn His
            20                  25                  30

Ala Met Gly Trp Phe Arg Gln Ala Pro Gly Lys Glu Arg Glu Phe Val
        35                  40                  45

Ala Ala Ile Ser Trp Thr Gly Leu Thr Thr Asn Tyr Ala Asp Ser Val
    50                  55                  60

Lys Gly Arg Phe Phe Ile Ser Arg Asp Asp Ala Glu Asn Thr Val Tyr
65                  70                  75                  80

Leu Gln Met Asn Ser Leu Glu Pro Glu Asp Thr Ala Val Tyr Tyr Cys
                85                  90                  95

Ala Ala Arg Gln Ser Gly Tyr Val Ser Lys Phe Val Asp Asp Tyr Gly
            100                 105                 110

Tyr Trp Gly Gln Gly Thr Gln Val Thr Val Ser Ser
        115                 120
```

<210> SEQ ID NO 8
<211> LENGTH: 124
<212> TYPE: PRT
<213> ORGANISM: Artificial sequence
<220> FEATURE:
<223> OTHER INFORMATION: Single domain antibody

<400> SEQUENCE: 8

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Asn
            20                  25                  30

Ala Met Gly Trp Phe Arg Gln Ala Pro Gly Lys Glu Arg Glu Phe Val
        35                  40                  45

Ala Ala Ile Ser Trp Thr Gly Leu Thr Thr Asn Tyr Ala Asp Ser Val
    50                  55                  60

Lys Gly Arg Phe Phe Ile Ser Arg Asp Asp Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Gln Ser Gly Tyr Ala Ser Lys Phe Leu Asp Glu Tyr Gly
            100                 105                 110

Tyr Trp Gly Gln Gly Thr Gln Val Thr Val Ser Ser
        115                 120
```

<210> SEQ ID NO 9
<211> LENGTH: 126
<212> TYPE: PRT
<213> ORGANISM: Artificial sequence
<220> FEATURE:
<223> OTHER INFORMATION: Single domain antibody

<400> SEQUENCE: 9

```
Gln Val Gln Leu Gln Glu Ser Gly Gly Gly Leu Val Gln Pro Gly Asp
```

-continued

```
1               5                   10                  15

Ser Leu Arg Leu Ser Cys Ala Ala Ser Gly Arg Thr Phe Ser Thr Tyr
            20                  25                  30

Ala Met Gly Trp Phe Arg Gln Ala Pro Gly Lys Glu Arg Glu Phe Val
        35                  40                  45

Ala Tyr Ile Ser Gln Leu Ser Leu Ser Thr Lys Tyr Ala Asp Ser Val
    50                  55                  60

Lys Gly Arg Phe Thr Val Ser Arg Asp Asp Ala Gln Asn Thr Leu Tyr
65                  70                  75                  80

Leu Gln Met Asn Ser Leu Arg Pro Glu Asp Thr Ala Val Tyr Tyr Cys
                85                  90                  95

Ala Thr Arg Ser Gln Asn Tyr Val Thr Thr Tyr Asp Gln Ser Arg Ala
            100                 105                 110

Tyr Asp Tyr Trp Gly Gln Gly Thr Gln Val Thr Val Ser Ser
        115                 120                 125
```

<210> SEQ ID NO 10
<211> LENGTH: 432
<212> TYPE: DNA
<213> ORGANISM: Artificial sequence
<220> FEATURE:
<223> OTHER INFORMATION: Single domain antibody

<400> SEQUENCE: 10

```
caggtgcagc tgcaggagtc tggggggaggc ttggtgcagc ctggggggtc tctgagactc     60

tcctgtgcag gctctggacg cactattagc aaccatgcca tgggctggtt ccgccaggct    120

ccagggaagg agcgcgagtt tgtagcagct attagctgga ctggacttac cacgaactat    180

gcagactccg tgaagggccg attcttcatc tccagagacg acgccgagaa cacggtgtat    240

ctgcaaatga acagcctgaa acctgaagac acggccgttt attactgtgc agcccgccag    300

tccggttacg tgtcgaaatt cgtcgatgac tatggctact ggggccaggg gacccaggtc    360

accgtctcct cagcggccgc atacccgtac gacgttccgg actacggttc ccaccaccat    420

caccatcact ag                                                         432
```

<210> SEQ ID NO 11
<211> LENGTH: 432
<212> TYPE: DNA
<213> ORGANISM: Artificial sequence
<220> FEATURE:
<223> OTHER INFORMATION: Single domain antibody

<400> SEQUENCE: 11

```
caggtgcagc tgcaggagtc tgggggagga ttggtgcagg ctggggactc tctgagactc     60

tcctgtgcag gctctggacg cactattagc aaccatgcca tgggctggtt ccgccaggct    120

ccagggaagg agcgcgagtt tgtagcagct attagctgga ctggacttac cacgaactat    180

gcagactccg tgaagggccg attcttcatc tccagagacg acgccgagaa cacggtgtat    240

ctgcaaatga acagcctgga acctgaagac acggccgttt attactgtgc agcccgccag    300

tccggttacg tgtcgaaatt cgtcgatgac tatggctact ggggccaggg gacccaggtc    360

accgtctcct cagcggccgc atacccgtac gacgttccgg actacggttc ccaccaccat    420

caccatcact ag                                                         432
```

<210> SEQ ID NO 12
<211> LENGTH: 432
<212> TYPE: DNA

<213> ORGANISM: Artificial sequence
<220> FEATURE:
<223> OTHER INFORMATION: Single domain antibody

<400> SEQUENCE: 12

```
caggtgcagc tgcaggagtc tgggggagga ttggtgcagg ctgggggctc tctgagactc     60

tcctgcgcag cctctggacg caccttcagt agtaatgcca tgggctggtt ccgccaggct    120

ccagggaagg agcgcgagtt tgtagcagct attagctgga ctggacttac cacgaactat    180

gcagactccg tgaagggccg attcttcatc tccagagacg acgccaagaa cacggtgtat    240

ctgcaaatga acagcctgaa acctgaagac acggccgttt attactgtgc agcccgccag    300

tccggttacg cgtcgaaatt cctcgatgag tatggctact ggggccaggg gacccaggtc    360

accgtctcct cagcggccgc atacccgtac gacgttccgg actacggttc ccaccaccat    420

caccatcact ag                                                         432
```

<210> SEQ ID NO 13
<211> LENGTH: 438
<212> TYPE: DNA
<213> ORGANISM: Artificial sequence
<220> FEATURE:
<223> OTHER INFORMATION: Single domain antibody

<400> SEQUENCE: 13

```
caggtgcagc tgcaggagtc tgggggagga ttggtgtagc ctggggactc tctgagactc     60

tcctgtgcag cctctggacg caccttcagt acctatgcca tgggctggtt ccgccaggct    120

ccagggaagg agcgtgagtt tgtagcctat attagtcaac ttagtttgag cacaaagtat    180

gcagactccg tgaagggccg attcaccgtc tccagagacg acgcccagaa cacgctgtat    240

ctgcagatga acagtctgag acctgaggac acggccgtgt attactgtgc cactaggagc    300

caaaattatg ttactactta cgatcagtcc agggcgtatg actactgggg ccaggggacc    360

caggtcaccg tctcctcagc ggccgcatac ccgtacgacg ttccggacta cggttcccac    420

caccatcacc atcactag                                                   438
```

<210> SEQ ID NO 14
<211> LENGTH: 10
<212> TYPE: PRT
<213> ORGANISM: Artificial sequence
<220> FEATURE:
<223> OTHER INFORMATION: CDR sequence

<400> SEQUENCE: 14

```
Gly Arg Thr Phe Ser Thr Tyr Ala Met Gly
1               5                   10
```

<210> SEQ ID NO 15
<211> LENGTH: 10
<212> TYPE: PRT
<213> ORGANISM: Artificial sequence
<220> FEATURE:
<223> OTHER INFORMATION: CDR sequence

<400> SEQUENCE: 15

```
Tyr Ile Ser Gln Leu Ser Leu Ser Thr Lys
1               5                   10
```

<210> SEQ ID NO 16
<211> LENGTH: 17
<212> TYPE: PRT
<213> ORGANISM: Artificial sequence
<220> FEATURE:
<223> OTHER INFORMATION: CDR sequence

<400> SEQUENCE: 16

```
Arg Ser Gln Asn Tyr Val Thr Thr Tyr Asp Gln Ser Arg Ala Tyr Asp
1               5                   10                  15

Tyr
```

<210> SEQ ID NO 17
<211> LENGTH: 357
<212> TYPE: PRT
<213> ORGANISM: Artificial sequence
<220> FEATURE:
<223> OTHER INFORMATION: VHH-MG fusion

<400> SEQUENCE: 17

```
Gln Val Gln Leu Gln Glu Ser Gly Gly Gly Leu Val Gln Pro Gly Gly
1               5                   10                  15

Ser Leu Arg Leu Ser Cys Ala Gly Ser Gly Arg Thr Ile Ser Asn His
            20                  25                  30

Ala Met Gly Trp Phe Arg Gln Ala Pro Gly Lys Glu Arg Glu Phe Val
        35                  40                  45

Ala Ala Ile Ser Trp Thr Gly Leu Thr Thr Asn Tyr Ala Asp Ser Val
    50                  55                  60

Lys Gly Arg Phe Phe Ile Ser Arg Asp Asp Ala Glu Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Gln Ser Gly Tyr Val Ser Lys Phe Val Asp Asp Tyr Gly
            100                 105                 110

Tyr Trp Gly Gln Gly Thr Gln Val Thr Val Ser Ser Glu Pro Arg Gly
        115                 120                 125

Pro Thr Ile Lys Pro Cys Pro Pro Cys Lys Cys Pro Ala Pro Asn Leu
    130                 135                 140

Leu Gly Gly Pro Ser Val Phe Ile Phe Pro Pro Lys Ile Lys Asp Val
145                 150                 155                 160

Leu Met Ile Ser Leu Ser Pro Ile Val Thr Cys Val Val Val Asp Val
                165                 170                 175

Ser Glu Asp Asp Pro Asp Val Gln Ile Ser Trp Phe Val Asn Asn Val
            180                 185                 190

Glu Val His Thr Ala Gln Thr Gln Thr His Arg Glu Asp Tyr Asn Ser
        195                 200                 205

Thr Leu Arg Val Val Ser Ala Leu Pro Ile Gln His Gln Asp Trp Met
    210                 215                 220

Ser Gly Lys Glu Phe Lys Cys Lys Val Asn Asn Lys Asp Leu Pro Ala
225                 230                 235                 240

Pro Ile Glu Arg Thr Ile Ser Lys Pro Lys Gly Ser Val Arg Ala Pro
                245                 250                 255

Gln Val Tyr Val Leu Pro Pro Pro Glu Glu Glu Met Thr Lys Lys Gln
            260                 265                 270

Val Thr Leu Thr Cys Met Val Thr Asp Phe Met Pro Glu Asp Ile Tyr
        275                 280                 285

Val Glu Trp Thr Asn Asn Gly Lys Thr Glu Leu Asn Tyr Lys Asn Thr
    290                 295                 300

Glu Pro Val Leu Asp Ser Asp Gly Ser Tyr Phe Met Tyr Ser Lys Leu
305                 310                 315                 320
```

```
Arg Val Glu Lys Lys Asn Trp Val Glu Arg Asn Ser Tyr Ser Cys Ser
                325                 330                 335

Val Val His Glu Gly Leu His Asn His His Thr Thr Lys Ser Phe Ser
            340                 345                 350

Arg Thr Pro Gly Lys
        355


<210> SEQ ID NO 18
<211> LENGTH: 342
<212> TYPE: PRT
<213> ORGANISM: Artificial sequence
<220> FEATURE:
<223> OTHER INFORMATION: porcine Fc domain

<400> SEQUENCE: 18

Val Ser Glu Thr Ser Pro Lys Ile Phe Pro Leu Thr Leu Gly Ser Ser
1               5                   10                  15

Glu Pro Ala Gly Tyr Val Val Ile Ala Cys Leu Val Arg Asp Phe Phe
            20                  25                  30

Pro Ser Glu Pro Leu Thr Val Thr Trp Ser Pro Ser Arg Glu Gly Val
        35                  40                  45

Ile Val Arg Asn Phe Pro Pro Ala Gln Ala Gly Gly Leu Tyr Thr Met
    50                  55                  60

Ser Ser Gln Leu Thr Leu Pro Val Glu Gln Cys Pro Ala Asp Gln Ile
65                  70                  75                  80

Leu Lys Cys Gln Val Gln His Leu Ser Lys Ser Ser Gln Ser Val Asn
                85                  90                  95

Val Pro Cys Lys Val Leu Pro Ser Asp Pro Cys Pro Gln Cys Cys Lys
            100                 105                 110

Pro Ser Leu Ser Leu Gln Pro Pro Ala Leu Ala Asp Leu Leu Leu Gly
        115                 120                 125

Ser Asn Ala Ser Leu Thr Cys Thr Leu Ser Gly Leu Lys Lys Ser Glu
    130                 135                 140

Gly Val Ser Phe Thr Trp Gln Pro Ser Gly Gly Lys Asp Ala Val Gln
145                 150                 155                 160

Ala Ser Pro Thr Arg Asp Ser Cys Gly Cys Tyr Ser Val Ser Ser Ile
                165                 170                 175

Leu Pro Gly Cys Ala Asp Pro Trp Asn Lys Gly Glu Thr Phe Ser Cys
            180                 185                 190

Thr Ala Ala His Ser Glu Leu Lys Ser Ala Leu Thr Ala Thr Ile Thr
        195                 200                 205

Lys Pro Lys Val Asn Thr Phe Arg Pro Gln Val His Leu Leu Pro Pro
    210                 215                 220

Pro Ser Glu Glu Leu Ala Leu Asn Glu Leu Val Thr Leu Thr Cys Leu
225                 230                 235                 240

Val Arg Gly Phe Ser Pro Lys Asp Val Leu Val Arg Trp Leu Gln Gly
                245                 250                 255

Gly Gln Glu Leu Pro Arg Asp Lys Tyr Leu Val Trp Glu Ser Leu Pro
            260                 265                 270

Glu Pro Gly Gln Ala Ile Pro Thr Tyr Ala Val Thr Ser Val Leu Arg
        275                 280                 285

Val Asp Ala Glu Asp Trp Lys Gln Gly Asp Thr Phe Ser Cys Met Val
    290                 295                 300

Gly His Glu Ala Leu Pro Leu Ala Phe Thr Gln Lys Thr Ile Asp Arg
305                 310                 315                 320
```

```
Leu Ala Gly Lys Pro Thr His Val Asn Val Ser Val Val Met Ala Glu
                325                 330                 335

Ala Glu Gly Ile Cys Tyr
            340


<210> SEQ ID NO 19
<211> LENGTH: 238
<212> TYPE: PRT
<213> ORGANISM: Artificial sequence
<220> FEATURE:
<223> OTHER INFORMATION: porcine Fc domain

<400> SEQUENCE: 19

Asp Pro Cys Pro Gln Cys Cys Lys Pro Ser Leu Ser Leu Gln Pro Pro
1               5                   10                  15

Ala Leu Ala Asp Leu Leu Leu Gly Ser Asn Ala Ser Leu Thr Cys Thr
            20                  25                  30

Leu Ser Gly Leu Lys Lys Ser Glu Gly Val Ser Phe Thr Trp Gln Pro
        35                  40                  45

Ser Gly Gly Lys Asp Ala Val Gln Ala Ser Pro Thr Arg Asp Ser Cys
    50                  55                  60

Gly Cys Tyr Ser Val Ser Ser Ile Leu Pro Gly Cys Ala Asp Pro Trp
65                  70                  75                  80

Asn Lys Gly Glu Thr Phe Ser Cys Thr Ala Ala His Ser Glu Leu Lys
                85                  90                  95

Ser Ala Leu Thr Ala Thr Ile Thr Lys Pro Lys Val Asn Thr Phe Arg
            100                 105                 110

Pro Gln Val His Leu Leu Pro Pro Pro Ser Glu Glu Leu Ala Leu Asn
        115                 120                 125

Glu Leu Val Thr Leu Thr Cys Leu Val Arg Gly Phe Ser Pro Lys Asp
    130                 135                 140

Val Leu Val Arg Trp Leu Gln Gly Gly Gln Glu Leu Pro Arg Asp Lys
145                 150                 155                 160

Tyr Leu Val Trp Glu Ser Leu Pro Glu Pro Gly Gln Ala Ile Pro Thr
                165                 170                 175

Tyr Ala Val Thr Ser Val Leu Arg Val Asp Ala Glu Asp Trp Lys Gln
            180                 185                 190

Gly Asp Thr Phe Ser Cys Met Val Gly His Glu Ala Leu Pro Leu Ala
        195                 200                 205

Phe Thr Gln Lys Thr Ile Asp Arg Leu Ala Gly Lys Pro Thr His Val
    210                 215                 220

Asn Val Ser Val Val Met Ala Glu Ala Glu Gly Ile Cys Tyr
225                 230                 235


<210> SEQ ID NO 20
<211> LENGTH: 333
<212> TYPE: PRT
<213> ORGANISM: Artificial sequence
<220> FEATURE:
<223> OTHER INFORMATION: porcine Fc domain

<400> SEQUENCE: 20

Ala Tyr Asn Thr Ala Pro Ser Val Tyr Pro Leu Ala Pro Cys Gly Arg
1               5                   10                  15

Asp Val Ser Asp His Asn Val Ala Leu Gly Cys Leu Val Ser Ser Tyr
            20                  25                  30

Phe Pro Glu Pro Val Thr Val Thr Trp Asn Ser Gly Ala Leu Ser Arg
```

```
        35                  40                  45

Val Val His Thr Phe Pro Ser Val Leu Gln Pro Ser Gly Leu Tyr Ser
    50                  55                  60

Leu Ser Ser Met Val Ile Val Ala Ala Ser Ser Leu Ser Thr Leu Ser
65                  70                  75                  80

Tyr Thr Cys Asn Val Tyr His Pro Ala Thr Asn Thr Lys Val Asp Lys
                85                  90                  95

Arg Val Asp Ile Glu Pro Pro Thr Pro Ile Cys Pro Glu Ile Cys Ser
            100                 105                 110

Cys Pro Ala Ala Glu Val Leu Gly Ala Pro Ser Val Phe Leu Phe Pro
        115                 120                 125

Pro Lys Pro Lys Asp Ile Leu Met Ile Ser Arg Thr Pro Lys Val Thr
    130                 135                 140

Cys Val Val Val Asp Val Ser Gln Glu Glu Ala Glu Val Gln Phe Ser
145                 150                 155                 160

Trp Tyr Val Asp Gly Val Gln Leu Tyr Thr Ala Gln Thr Arg Pro Met
                165                 170                 175

Glu Glu Gln Phe Asn Ser Thr Tyr Arg Val Val Ser Val Leu Pro Ile
            180                 185                 190

Gln His Gln Asp Trp Leu Lys Gly Lys Glu Phe Lys Cys Lys Val Asn
        195                 200                 205

Asn Lys Asp Leu Leu Ser Pro Ile Thr Arg Thr Ile Ser Lys Ala Thr
    210                 215                 220

Gly Pro Ser Arg Val Pro Gln Val Tyr Thr Leu Pro Pro Ala Trp Glu
225                 230                 235                 240

Glu Leu Ser Lys Ser Lys Val Ser Ile Thr Cys Leu Val Thr Gly Phe
                245                 250                 255

Tyr Pro Pro Asp Ile Asp Val Glu Trp Gln Ser Asn Gly Gln Gln Glu
            260                 265                 270

Pro Glu Gly Asn Tyr Arg Thr Thr Pro Pro Gln Gln Asp Val Asp Gly
        275                 280                 285

Thr Tyr Phe Leu Tyr Ser Lys Leu Ala Val Asp Lys Val Arg Trp Gln
    290                 295                 300

Arg Gly Asp Leu Phe Gln Cys Ala Val Met His Glu Ala Leu His Asn
305                 310                 315                 320

His Tyr Thr Gln Lys Ser Ile Ser Lys Thr Gln Gly Lys
                325                 330


<210> SEQ ID NO 21
<211> LENGTH: 329
<212> TYPE: PRT
<213> ORGANISM: Artificial sequence
<220> FEATURE:
<223> OTHER INFORMATION: porcine Fc domain

<400> SEQUENCE: 21

Ala Pro Ser Val Tyr Pro Leu Ala Pro Cys Gly Arg Asp Val Ser Asp
1               5                   10                  15

His Asn Val Ala Leu Gly Cys Leu Val Ser Ser Tyr Phe Pro Glu Pro
            20                  25                  30

Val Thr Val Thr Trp Asn Ser Gly Ala Leu Ser Arg Val Val His Thr
        35                  40                  45

Phe Pro Ser Val Leu Gln Pro Ser Gly Leu Tyr Ser Leu Ser Ser Met
    50                  55                  60

Val Ile Val Ala Ala Ser Ser Leu Ser Thr Leu Ser Tyr Thr Cys Asn
```

-continued

```
65                  70                  75                  80

Val Tyr His Pro Ala Thr Asn Thr Lys Val Asp Lys Arg Val Asp Ile
                85                  90                  95

Glu Pro Pro Thr Pro Ile Cys Pro Glu Ile Cys Ser Cys Pro Ala Ala
            100                 105                 110

Glu Val Leu Gly Ala Pro Ser Val Phe Leu Phe Pro Pro Lys Pro Lys
        115                 120                 125

Asp Ile Leu Met Ile Ser Arg Thr Pro Lys Val Thr Cys Val Val Val
    130                 135                 140

Asp Val Ser Gln Glu Glu Ala Glu Val Gln Phe Ser Trp Tyr Val Asp
145                 150                 155                 160

Gly Val Gln Leu Tyr Thr Ala Gln Thr Arg Pro Met Glu Glu Gln Phe
                165                 170                 175

Asn Ser Thr Tyr Arg Val Val Ser Val Leu Pro Ile Gln His Gln Asp
            180                 185                 190

Trp Leu Lys Gly Lys Glu Phe Lys Cys Lys Val Asn Asn Lys Asp Leu
        195                 200                 205

Leu Ser Pro Ile Thr Arg Thr Ile Ser Lys Ala Thr Gly Pro Ser Arg
    210                 215                 220

Val Pro Gln Val Tyr Thr Leu Pro Pro Ala Trp Glu Glu Leu Ser Lys
225                 230                 235                 240

Ser Lys Val Ser Ile Thr Cys Leu Val Thr Gly Phe Tyr Pro Pro Asp
                245                 250                 255

Ile Asp Val Glu Trp Gln Ser Asn Gly Gln Gln Glu Pro Glu Gly Asn
            260                 265                 270

Tyr Arg Thr Thr Pro Pro Gln Gln Asp Val Asp Gly Thr Tyr Phe Leu
        275                 280                 285

Tyr Ser Lys Leu Ala Val Asp Lys Val Arg Trp Gln Arg Gly Asp Leu
    290                 295                 300

Phe Gln Cys Ala Val Met His Glu Ala Leu His Asn His Tyr Thr Gln
305                 310                 315                 320

Lys Ser Ile Ser Lys Thr Gln Gly Lys
                325
```

IMMUNOGLOBULIN SINGLE DOMAIN ANTIBODIES FOR DELIVERY OF MUCOSAL VACCINES

CROSS-REFERENCES TO RELATED APPLICATIONS

This application is a national-stage application under 35 U.S.C. § 371 of International Application No. PCT/EP2021/050798, filed Jan. 15, 2021, which International Application claims benefit of priority to European Patent Application No. 20152428.7, filed Jan. 17, 2020.

FIELD OF THE INVENTION

The present invention relates to single-domain antibodies that specifically bind aminopeptidase N (APN), and more in particular to polypeptides and nucleic acids encoding such polypeptides; to methods for preparing such polypeptides; to compositions and in particular to pharmaceutical compositions that comprise such polypeptides, for prophylactic, therapeutic or diagnostic purposes. In particular, the single-domain antibodies of the present invention are capable of targeting a moiety to a mucosal surface.

BACKGROUND OF THE INVENTION

The vast majority of pathogens and external noxious substances enter the body through the mucosal surfaces of the respiratory, gastrointestinal (GI) and urogenital tracts, and thus mucosal immunity is of paramount importance to counter infection. Currently, needle-free oral vaccine delivery is the most attractive route of administration for protection against intestinal pathogens, because it offers many advantages, such as ease of administration, no risk of blood-borne infection and practicality for mass vaccination. In contrast to subunit vaccines, only live attenuated vaccines or inactivated pathogen particles have been found to be effective in stimulating an efficient immune response. However, because of the safety issues associated with orally delivered live attenuated or inactivated pathogens, only a handful of such vaccines have been approved. On the other hand, subunit vaccines are considered to be safe because they do not contain the life component of the pathogen, but poor transport of vaccine antigens across the intestinal epithelium to reach the underlying immune inductive sites resulting in a poor immune response pose a major hurdle to the development of oral vaccines. Enterocytes or absorptive villus epithelial cells constitute 90% of all intestinal epithelium and they possess phagocytosis and transcytosis capacities to transport enteric pathogens or macromolecules across the epithelial barrier [1]. Therefore, antigen targeting to transcytotic receptors on enterocytes is an interesting approach for vaccine delivery and inducing a strong mucosal as well as systemic immune response against intestinal pathogens [2].

In the recent past, aminopeptidase N (APN) has been identified as a receptor for F4 fimbriae that is expressed on a variety of cells including small intestinal enterocytes and antigen presenting cells (APCs), but not on epithelial cells of other parts of the GI tract [3]. Oral immunization with APN-specific polyclonal antibodies triggered mucosal immunity [3, WO09/103555]. Moreover, functionalization of microparticles with APN-specific mouse monoclonal antibodies also increased uptake of these particles by the intestinal epithelium and triggered systemic immune responses [4]. These findings suggest that an APN-specific delivery agent conjugated with a vaccine antigen could be an interesting strategy to elicit a stronger intestinal immune response. To date, several targeting mechanisms have been identified, such as antibodies, cell-mediated targeting (DC immunotherapy, T cell adoptive transfer), and chemical conjugation of the antigen to small molecules such as glycans and amino acids [5]. Because of their strong affinity and specificity, antibodies are the ideal proteins to which an antigen of interest can be genetically fused for targeting the APN-expressing enterocytes. Different antibody formats can be used, such as a monoclonal antibody (mAb), the single-chain variable fragments (scFvs), or the variable domain of heavy-chain-only antibodies (VHH, also known as Nanobody®). Although conventional mAbs have originally been preferred as a targeting vehicle, their production fused with the antigens turned out to be cumbersome and time-consuming. In addition, their structural complexity hampers their use as potential ligands. Therefore, other simpler forms such as scFvs and VHHs were considered as alternative approaches to full-sized antibodies. Although the advances in antibody engineering made it possible to easily design and clone scFv genes based on the targeting performance of mAbs, the stability and accumulation of the synthetic scFv proteins vary heavily, depending on several factors, including the unpredictable length of the requisite linker to obtain proper folding and the assembly of the two variable domains, and this often restricted scFv targeting applications [6, 7]. On the other hand, the VHH immunoglobulin domain is only a 15 kDa variable fragment derived from the camelid heavy-chain only antibody [8]. Unlike scFv, VHH contains its antigen-binding properties in a single domain rather than in two variable domains in conventional antibodies and derived scFvs, while retaining similar affinity. Owing to its peculiar properties such as small size, ease of production, good thermostability and efficient tissue penetration, VHH has received great interest for various applications compared to classical antibodies [9-11].

The present invention provides VHHs and their application as a carrier for targeted delivery to the gut epithelium e.g. to induce strong mucosal immune responses.

SUMMARY OF THE INVENTION

The present invention identified a family of VHHs, able to be produced to high levels and being stable. Said family of VHHs not only bind APN, but are efficiently endocytosed by cell lines and in loops of the porcine gut under physiological conditions, and notably, are capable of eliciting systemic and intestinal IgA responses, in particular after oral administration. The polypeptides of the present invention can be used as a delivery vehicle targeting the APN receptor and for efficiently delivering molecules specifically to APN expressing mucosa, more particular to the (small) intestines. Moreover, the polypeptides of the invention pass the epithelial barrier after oral administration to pigs, showing its usefulness as a carrier for targeting heterologous compounds/antigens towards the intestinal mucosal immune system.

In one embodiment, the polypeptide of the invention comprises at least one immunoglobulin single variable domain (ISVD), wherein said ISVD comprises 3 complementarity determining regions (CDR1 to CDR3 respectively), in which (i) CDR1 is chosen from the group consisting of SEQ ID NOs: 1, and amino acid sequences that have 1, 2 or 3 amino acid difference(s) with SEQ ID NO: 1, in particular 2 amino acids differences, more in particular 1 amino acid difference;

(ii) CDR2 is chosen from the group consisting of SEQ ID NOs: 3, and amino acid sequences that have 1, 2 or 3 amino acid difference(s) with SEQ ID NO: 3, in particular 2 amino acids differences, more in particular 1 amino acid difference;

and (iii) CDR3 is chosen from the group consisting of SEQ ID NO: 4, and amino acid sequences that have 1, 2 or 3 amino acid difference(s) with SEQ ID NO: 4, in particular 2 amino acids differences, more in particular 1 amino acid difference.

More specific, (i) CDR1 is chosen from SEQ ID NO: 1 or 2; (ii) CDR2 is SEQ ID NO: 3; and (iii) CDR3 is chosen from SEQ ID NO: 4 or 5. A particular polypeptide according to the invention comprises a CDR1, CDR2 and CDR3 combination that is chosen from:

CDR1 is SEQ ID NO: 1, CDR2 is SEQ ID NO: 3, and CDR3 is SEQ ID NO: 4; or

CDR1 is SEQ ID NO: 2, CDR2 is SEQ ID NO: 3, and CDR3 is SEQ ID NO: 5.

More in particular, the ISVD according to the invention consists of or essentially consists of 4 framework regions (FR1 to FR4, respectively) and the herein provided complementarity determining regions CDR1, CDR2 and CDR3.

In one embodiment, the present invention provides a polypeptide comprising or consisting of SEQ ID NO: 6, or a polypeptide which has at least 80% sequence identity to SEQ ID NO: 6, such as e.g. SEQ ID NO: 7 or SEQ ID NO: 8.

In a further embodiment, an APN binding construct comprising at least one polypeptide of the invention is provided. Said construct may contain other moieties linked to the immunoglobulin single variable domain. Said further moieties may bind to APN or not. In a particular embodiment, the construct further comprises an Fc domain and/or a further diagnostic or therapeutic moiety, e.g. a bio-active compound.

In another embodiment, the immunoglobulin single variable domains are not provided as such, but are provided as nucleic acids, i.e. isolated or recombinant nucleic acid molecules encoding the polypeptides as herein described. Furthermore, vectors or host cells are provided containing such nucleic acids. Typically, such host cells will have been transformed or transfected with the nucleic acids. A particular use that is envisaged for these host cells is the production of the immunoglobulin single variable domain or polypeptide of the invention. Thus, host cells transformed or transfected with the nucleic acid molecules encoding polypeptides provided herein can be used for production of the immunoglobulin single variable domain.

According to a further aspect, the polypeptides, nucleic acids or constructs provided herein are for use in medicine, in particular for use as a medicament, either human or veterinary. According to another embodiment, the polypeptides (or nucleic acids encoding them) are provided for use in therapeutic treatment or prevention of (gastro)intestinal disease.

The polypeptide of the invention may be provided as protein (as immunoglobulin single variable domain, as part of an APN binding construct, chimeric molecule or pharmaceutical composition) or may be administered as a nucleic acid molecule encoding said immunoglobulin single variable domain, or as a vector comprising such nucleic acid molecule. Different routes of administration can be envisaged. As non-limiting examples, the polypeptide may be administered systemically, orally or intranasally, but in particularly orally. In case the immunoglobulin single variable domain is provided as a nucleic acid or vector, it is particularly envisaged that the immunoglobulin single variable domain is administered through gene therapy. A specific embodiment provides the polypeptide, the construct, the chimeric molecule, or the pharmaceutical composition for use in vaccination, in particular mucosal vaccination.

In one embodiment, the invention provides a pharmaceutical composition comprising the polypeptide, the construct or chimeric molecule, the nucleic acid or the host cell as described herein, and a pharmaceutically acceptable carrier, excipient and/or diluent. In particular, the pharmaceutical composition is a vaccine, more in particular an oral vaccine, i.e. a vaccine suitably formulated for oral delivery.

The invention further encompasses a method of treating or preventing an intestinal disease or disorder in a subject, the method comprising administering the polypeptide, the construct, the chimeric molecule or the pharmaceutical composition, to said subject in an amount effective to treat, reduce or prevent at least one symptom of said disease or disorder.

In another embodiment, the invention covers the polypeptide, the construct or chimeric molecule, the nucleic acid or the host cell as described herein for diagnostic use, e.g. for use in bio-imaging or for use in a competition assay. Moreover, the polypeptide, the construct or chimeric molecule can be used in an in vitro method for identifying and obtaining a compound or organism (e.g. a virus) capable of crossing the mucosal barrier in a subject, said method comprising: a) incubating a source, cell or cell line containing APN or a functional fragment thereof with the compound or organism to be tested; and b) determine the capability of said molecule to compete with the polypeptide or chimeric molecule as provided herein.

Also provided is a method to produce the polypeptide of the invention, said method comprising the steps of:

introducing the nucleic acid encoding the polypeptide in an expression system, in particular *Pichia pastoris*, and purifying the expressed polypeptide.

BRIEF DESCRIPTION OF THE FIGURES

(FIG. 1B) Efficiency of obtaining error-free clones via the BioXP cloning system. The probability to obtain error-free clones was 77% when one clone was screened and 97% when two clones were screened per construct via sequencing.

(FIG. 2A) ELISA plates were coated with APN and incubated with the culture medium. APN binding of VHH-MG is depicted as O.D. values of the colorimetric reaction. (FIG. 2B) Flow cytometry screening for the VHH-MGs that bind to full-length APN expressed on the membrane of APN-transfected BHK21 (BHK21-APN, gray bars) and APN-transfected IPEC-J2 (IPEC-J2-APN, black bars). IMM013 (murine IgG1) is the positive control. IgG1 isotype, V2-MG and D3-MG are the negative controls. V2-MG and D3-MG fusions contain a VHH (V2 and D3, respectively) that binds an irrelevant target. The graph shows the mean fluorescence intensity (MFI).

(FIG. 3A) Size exclusion chromatography (SEC) profile of six different VHH-MG fusions after protein A purification, labeled with its respective name at the top right corner. The arrows indicate the position and molecular weight of ~80 kDa, corresponding to monomeric VHH-MG fusions assembled by disulfide bridges between two VHH-MG polypeptides (~40 kDa each). (FIG. 3B) SDS-PAGE analysis of pooled fractions of the 80-kDa peak after SEC on 4-20% polyacrylamide gel under both reducing (left) and non-reducing (right) conditions. The expected position of the intact full-length polypeptide is indicated by the arrowhead for monovalent VHH-MG (~40 kDa) in reducing conditions and by the arrow for bivalent VHH-MG (~80 kDa) in non-reducing conditions. M, molecular weight marker (kDa). (Yield-3L94-MG: 2.7 mg/L; 2L48-MG: 2.3 mg/L; 2L69-MG: 1.9 mg/L; 2L65-MG: 5.9 mg/L; 2L22-MG: 8 mg/L; 2L46-MG: 1.4 mg/L).

(FIG. 5A) APN binding ELISA with purified VHH-MG fusions. A three-fold dilution series of purified VHH-MGs were incubated on an APN-coated microtiter plate and probed with anti-mouse IgG conjugated with horse radish peroxidase. The binding of VHH-MG to immobilized antigen is depicted as OD (492 nm) values. IMM013 is a positive and GBP-MG is a negative control. The background threshold was determined as twice the OD (492 nm) value of the negative control. (FIG. 5B) Binding of the VHH-MG fusions to APN expressing cells determined by flow cytometry. Graph shows the number of APN-positive cells that bind to VHH-MG at the indicated concentration (μg/ml).

(FIG. 6A) design of the oral immunization experiment. (FIG. 6B) mouse IgG2a-specific serum IgG and IgA responses upon oral immunization of piglets (n=4/group) with 1 mg VHH-MG 2L65 and 3L94 and an equimolar amount irrelevant mouse IgG2a. dppi: days post primary immunization; OD: optical density. Data are presented as the mean+sd. *, $p<0.05$ to IgG2a (Friedman). (FIG. 6C) the amount of circulating mouse IgG2a-specific IgG and IgA secreting cells at the indicating time points. ASC: antibody secreting cells. , $p<0.01$ to day 0; A, $p<0.05$ to IgG2a (Friedman). (FIG. 6**D) the amount of small intestinal mouse IgG2a-specific IgG and IgA secreting cells at d28 post primary immunization. MLN: mesenteric lymph nodes; JLP: jejunal lamina propria; JPP: jejunal Peyer's patches; ILP: ileal lamina propria; IPP: ileal Peyer's patches. *, $p<0.05$ (Holm-Sidak).

FIG. 8: Representative amino acid and nucleic acid sequences of the polypeptides of the invention. CDR are underlined.

FIG. 9: Amino acid and nucleic acid sequence of the VHH-Fc mouse IgG2a fusion construct (2L65-MG fusion). The sequence of the 2L65 VHH is in bold. The hinge sequence is underlined.

FIGS. 10A-10D: (FIG. 10A) Amino acid sequence of a part of porcine IgA (AAA65943.1; U12594.1); (FIG. 10B) hinge-CH2-CH3 fragment of porcine IgA; (FIG. 10C) Amino acid sequence of a part of the porcine IgG3 (EU372658.1); (FIG. 10D) CH1-hinge-CH2-CH3 fragment of porcine IgG3 (the CH1 domain starts at position 5).

DESCRIPTION OF THE INVENTION

Figure 1A:
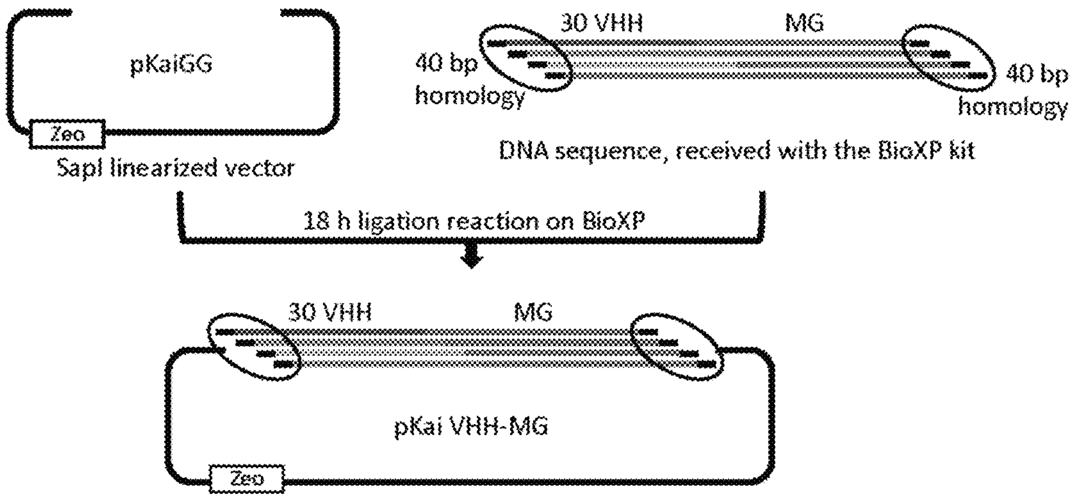
FIGS. 1A and 1B: Schematic representation of the BioXp™ 3200 System-based Gibson cloning strategy to efficiently obtain VHH-MG (variable domain of heavy chain-only antibody fused to Fc domain of murine IgG) fusions (FIG. 1A). The 40 bp at the ends of the VHH-MG fusion fragments are homologous with the ends of the SapI-linearized pKaiGG vector. MG represents the Fc domain of Mouse IgG. VHH-MG fragments were synthesized and ligated into SapI-digested pKaiGG in an overnight run on the BioXP system. DH5a cells were transformed with ligation samples and transformants were screened on Zeocin (Zeo)-supplemented medium. Subsequently, DNA was isolated from four randomly selected clones and analyzed by restriction digestion or colony PCR and sequencing to screen for positive clones.

Unless indicated or defined otherwise, all terms used have their usual meaning in the art, which will be clear to the skilled person.

As used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term". The term "about" or "approximately" as used herein means within 20%, preferably within 15%, more preferably within 10%, and most preferably within 5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

The term "sequence" as used herein (for example in terms like "immunoglobulin sequence", "antibody sequence", "variable domain sequence", "VHH sequence" or "protein sequence"), should generally be understood to include both the relevant amino acid sequence as well as nucleic acids or nucleotide sequences encoding the same, unless the context requires a more limited interpretation. A nucleic acid or amino acid sequence is considered to be "(in) (essentially) isolated (form)"—for example, compared to the reaction medium or cultivation medium from which it has been obtained—when it has been separated from at least one other component with which it is usually associated in said source or medium, such as another nucleic or amino acid, another protein/polypeptide, another biological component or macromolecule or at least one contaminant, impurity or minor component.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein. Alternatively, the degree of sequence identity between two amino acid sequences may be calculated using a known computer algorithm, such as those mentioned above for determining the degree of sequence identity for nucleotide sequences, again using standard settings.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species.

Unless indicated otherwise, the terms "immunoglobulin" and "immunoglobulin sequence" are used as a general term to include both the full-size antibody. An "immunoglobulin single variable domain" or "ISVD" is an antibody fragment consisting of a single variable antibody domain. Like a whole antibody, it is able to bind selectively to a specific antigen. With a molecular weight of only 12-18 kDa, ISVDs are much smaller than conventional antibodies (150-160 kDa) which are composed of two heavy and two light protein chains, and even smaller than Fab fragments (~50 kDa, one light chain and half a heavy chain) and single chain variable fragments (~25 kDa, two variable domains, one from a light and one from a heavy chain). Generally, an ISVD will have an amino acid sequence comprising 4 framework regions (FR1 to FR4) and 3 complementarity determining regions (CDR1 to CDR3), preferably according to the following formula: FR1-CDR1-FR2-CDR2-FR3-CDR3-FR4. The antigen binding site of an ISVD is formed by no more than three CDRs. The term "ISVD", as used herein, includes variable domains of camelid heavy chain antibodies (VHHs), also referred to as Nanobodies®, domain antibodies (dAbs), and ISVDs derived from shark (IgNAR domains).

Preferred framework sequences are outlined for example in FIG. 8 and can be used in an ISVD of the invention. Preferably, the CDRs depicted in Table 2 are matched with the respective framework regions of the same ISVD construct.

The term "immunoglobulin single variable domain" is interchangeably used with "single variable domain". As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit). In one embodiment, the immunoglobulin single variable domain is a VHH sequence.

An APN binder of the invention may be an immunoglobulin, such as an immunoglobulin single variable domain, derived in any suitable manner and from any suitable source, and may for example be naturally occurring VHH sequences (i.e., from a suitable species of Camelid) or synthetic or semi-synthetic amino acid sequences, including but not limited to "humanized" VHH sequences, "camelized" immunoglobulin sequences (and in particular camelized heavy chain variable domain sequences), as well as Nanobodies® that have been obtained by techniques such as affinity maturation (for example, starting from synthetic, random or naturally occurring immunoglobulin sequences), CD grafting, veneering, combining fragments derived from different immunoglobulin sequences, PCR assembly using overlapping primers, and similar techniques for engineering immunoglobulin sequences well known to the skilled person; or any suitable combination of any of the foregoing.

More in particular, the invention provides polypeptides, in particular specifically binding APN, comprising at least one immunoglobulin single variable domain that is an amino acid sequence with the (general) structure FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively. In one embodiment of the invention, said ISVD has at least 80%, preferably at least 85%, more preferably at least 90%, even more preferably at least 92% amino acid identity with at least one of the amino acid sequences of SEQ ID NOs: 6-8 (see FIG. 8—CDR are underlined), in particular with SEQ ID NO: 6.

As used herein "represented by" in the context of any SEQ ID NO is equivalent to "comprises or consists of" said SEQ ID NO and preferably equivalent to "consists of" said SEQ ID NO. A "VHH family" or "family" as used in the present specification refers to a group of VHH sequences that have identical lengths (i.e. they have the same number of amino acids within their sequence) and of which the amino acid sequence has a sequence identity of 80% or more (e.g. 85%, 90%, 91%, 92%, 93%, 94%, 95%, 96%, 97%, 98% or more).

In one embodiment, the equivalent sequence refers to an amino acid substitution which is preferably a conservative amino acid substitution (as defined herein); and/or said amino acid sequence preferably only contains amino acid substitutions, and no amino acid deletions or insertions, compared to the herein identified amino acid sequence(s); and/or an amino acid sequence that has 3, 2 or only 1 "amino acid difference(s)" (as defined herein) with one of the herein identified amino acid sequence(s). More particular, the equivalent sequence has an amino acid substitution being preferably a conservative amino acid substitution (as defined herein); and/or said amino acid sequence preferably only contains amino acid substitutions, and no amino acid deletions or insertions, compared to the herein identified amino acid sequence(s).

The terms "epitope" and "antigenic determinant", which can be used interchangeably, refer to the part of a macromolecule, such as a polypeptide or protein that is recognized by antigen-binding molecules, such as immunoglobulins, conventional antibodies, immunoglobulin single variable domains and/or polypeptides of the invention, and more particularly by the antigen-binding site of said molecules. Epitopes define the minimum binding site for an immunoglobulin, and thus represent the target of specificity of an immunoglobulin. An amino acid sequence (such as an immunoglobulin single variable domain, an antibody, a polypeptide of the invention, or generally an antigen binding protein or polypeptide or a fragment thereof) that can "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g., "anti"-APN).

The affinity denotes the strength or stability of a molecular interaction. The affinity is commonly given as by the $K_D$, or dissociation constant, which has units of mol/liter (or M). The affinity can also be expressed as an association constant, KA, which equals $1/K_D$ and has units of $(mol/liter)^{-1}$ (or $M^{-1}$). The $K_D$ for biological interactions which are considered meaningful (e.g. specific) are typically in the range of $10^{-12}$M (0.001 nM) to $10^{-5}$M (10000 nM). The stronger an interaction is, the lower is its $K_D$.

The affinity of a molecular interaction between two molecules can be measured via different techniques known per se, such as the well-known surface plasmon resonance (SPR) biosensor technique (see for example Ober et al. [12]) where one molecule is immobilized on the biosensor chip and the other molecule is passed over the immobilized molecule under flow conditions yielding kon, koff measurements and hence KD (or KA) values. This can for example be performed using the well-known BIACORE® instruments (Pharmacia Biosensor AB, Uppsala, Sweden). Kinetic Exclusion Assay (KINEXA®) [13] measures binding events in solution without labeling of the binding partners and is based upon kinetically excluding the dissociation of a complex. In-solution affinity analysis can also be performed using the GYROLAB® immunoassay system, which provides a platform for automated bioanalysis and rapid sample turnaround [14].

The term "specificity" refers to the number of different types of antigens or antigenic determinants to which a particular antigen-binding molecule or antigen-binding protein (such as an ISVD or polypeptide of the invention) molecule can bind. The specificity of an antigen-binding protein can be determined based on affinity and/or avidity. Typically, antigen-binding proteins (such as the ISVDs and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less. Any $K_D$ value greater than $10^{-4}$ mol/liter (or any KA value lower than $10^4$ liter/mol) is generally considered to indicate non-specific binding. Preferably, a monovalent ISVD of the invention will bind to the desired antigen with an affinity about or less than 10 μM, in particular about or less than 5 μM, more in particular less than 1 μM, such as e.g. less than 500 nM, more specific less than 200 nM, even more specific less than 10 nM, such as less than 500 pM, such as e.g., between 10 and 5 pM or less.

Specific binding of an antigen-binding protein, such as an ISVD, to an antigen or antigenic determinant can be determined in any suitable manner known to the skilled person, including, for example, saturation binding assays and/or competitive binding assays, such as radio-immunoassays (RIA), enzyme immunoassays (EIA) and sandwich competition assays, and the different variants thereof known per se in the art; as well as the other techniques mentioned herein and preferably by flow cytometry or surface plasmon resonance.

In one embodiment, the binding of polypeptides to pig APN (pAPN) was determined via ELISA and to pAPN-expressing cells via flow cytometry. However, because binding to immobilized antigen may not be equivalent to binding to the cell membrane, flow cytometry data was the most reliable. It showed binding to the full-length protein in its native form that is expressed on the biological membrane.

Moreover, we observed a clear correlation with the binding on intestinal tissue that further confirmed the flow cytometry data.

In one embodiment, the present invention provides a polypeptide specifically binding APN and furthermore showing specific uptake by cells via the APN receptor, in particular by APN expressing cells, more in particular by enterocytes. As used herein, "enterocytes", or intestinal absorptive cells (also referred to as absorptive villus epithelial cells), are epithelial cells which line the inner surface of the small and large intestines and possess phagocytosis and transcytosis capacities to transport enteric pathogens or macromolecules across the epithelial barrier.

"Aminopeptidase N (APN)" (also known as CD13, ANPEP, PEPN, alanyl aminopeptidase) is a type II membrane glycoprotein, which belongs to the family of membrane-bound metalloproteases and is expressed in a variety of tissues among which the intestinal brush border membranes.

Relevant structural information for APN may be found, for example, at UniProt or GenBank Accession Numbers as depicted in the Table 1 below.

TABLE 1

| Protein Accession No. | cDNA Accession No. | Organism |
|---|---|---|
| P15145.4 | NM_214277 (version: NM_214277.1) | *Sus scrofa* |
| P15144.4 | NM_001150 (version: NM_001150.3) | *Homo sapiens* |
| P79143.2 | NM_001146034 (version: NM_001146034.1) | *Canis lupus familiaris* |
| P79171.3 | NM_001009252 (version: NM_001009252.2) | *Felis catus* |
| | GDHK01043038.1 | *Equus caballus* |
| P79098.4 | NM_001075144 (version: NM_001075144.1) | *Bos Taurus* |

As used herein the "APN" or "CD13" polypeptide is meant to be a protein encoded by a mammalian APN gene, including allelic variants as well as biologically active fragments thereof containing conservative or non-conservative changes as well as artificial proteins that are substantially identical, i.e. at least 70%, 75%, 80%, 85%, 87%, 89%, 90%, 92%, 93%, 94%, 95%, 96%, 97%, 98%, or 99% identical to any one of the aforementioned APN polypeptides. In a particular embodiment the APN polypeptide is at least 70%, 75%, 80%, 85%, 87%, 89%, 90%, 92%, 93%, 94%, 95%, 96%, 97%, 98%, or 99% identical to the porcine or pig APN (*Sus scrofa*; Accession No. ADX53333.1). In a further embodiment, the APN polypeptides as defined herein, are further characterized in that they are glycosylated.

By analogy, the "APN" or "CD13" polynucleotide is meant to include allelic variants as well as biologically active fragments thereof containing conservative or non-conservative changes as well as any nucleic acid molecule that is substantially identical, i.e. at least 70%, 75%, 80%, 85%, 87%, 89%, 90%, 92%, 93%, 94%, 95%, 96%, 97%, 98%, or 99% identical to any one of the aforementioned APN encoding polynucleotides.

In a particular embodiment the APN polynucleotide is at least 70%, 75%, 80%, 85%, 87%, 89%, 90%, 92%, 93%, 94%, 95%, 96%, 97%, 98%, or 99% identical to the nucleic acid molecule encoding for porcine APN (Genbank Accession No HQ824547.1).

In one embodiment, the polypeptide of the invention specifically binds to and is internalized by mammalian intestinal APN, in particular porcine APN, more in particular porcine intestinal APN, more in particular expressed on epithelial cells or enterocytes present in the small intestine, said APN comprising the amino acid sequence represented by protein accession No. ADX53333.1. The unique data in the present invention demonstrate that after oral delivery the polypeptide not only binds APN, but also leads to endocytosis (transport into the cell) by the intestinal enterocytes and subsequent transcytosis (transport across the interior of the cell) through the epithelial barrier with appropriate presentation to the mucosal immune system.

APN expressing cells can be used to determine uptake or internalization of the polypeptide of the invention. The "expression" generally refers to the process by which polynucleotides are transcribed into mRNA and/or the process by which the mRNA is subsequently translated into peptides, polypeptides or proteins. APN expression may be facilitated or increased by methods that involve the introduction of exogenous nucleic acid into the cell. Such a cell may comprise a polynucleotide or vector in a manner that permits expression of an encoded APN polypeptide. Polynucleotides that encode APN as provided herein may be introduced into the host cell as part of a circular plasmid, or as linear DNA comprising an isolated protein-coding region, or in a viral vector. Methods for introducing exogenous nucleic acid into the host cell well known and routinely practiced in the art include transformation, transfection, electroporation, nuclear injection, or fusion with carriers such as liposomes, micelles, ghost cells, and protoplasts. Host cell systems of the invention include plant, invertebrate and vertebrate cells systems.

Cells to be used for studying the internalization are primary cells isolated from small intestinal epithelial tissue, such as for example enterocyte preparations; or continuous cells including recombinant cell lines expressing APN, in particular porcine intestinal epithelial cells (IPEC-J2, IPEC-I, IPI-2i), baby hamster kidney (BHK) cells (e.g. BHK21 cells), or "mini-intestines" derived either from adult ISCs (enteroids/organoids) or from induced pluripotent stem cells (iPSCs)(organoids). Further cells may include, but are not limited to, the following: insect cells, porcine kidney (PK) cells, porcine kidney cortex (SK-RST) cells, feline kidney (FK) cells, *Felis catus* whole foetus cells (Fcwf-4), swine testicular (ST) cells, African green monkey kidney cells (MA-104, MARC-145, VERO, and COS cells), Chinese hamster ovary (CHO) cells, human 293 cells, and murine 3T3 fibroblasts, human colon carcinoma epithelial (CaCo2) cells, human lymphoblast (Kasumi-3), human myeloblast (Kasumi-4), human myeloblast (Kasumi-6), human basophil cell line (KU812), human B lymphoblast (SUP-B15), human epithelial kidney cortex cells (WT 9-7, WT 9-12). Insect host cell culture systems may also be used for the expression of the polypeptides according to the invention.

In said context, the choice of a suitable expression vector for expression of the polypeptides according to the invention will of course depend upon the specific host cell to be used, and is within the skill of the ordinary artisan. Examples of suitable expression vectors include pSport and pcDNA3 (Invitrogen), pCMV-Script (Stratagene), and pSVL (Pharmacia Biotech). Expression vectors for use in mammalian host cells may include transcriptional and translational control sequences derived from viral genomes. Commonly used promoter sequences and modifier sequences which may be used in the present invention include, but are not limited to, those derived from human cytomegalovirus (CMV), Rous sarcoma virus (RSV), Adenovirus 2, Polyoma virus, and Simian virus 40 (SV40).

As an alternative, uptake or internalization of polypeptides can be determined by using porcine intestinal tissue in a gut ligated loop experiment, as is disclosed in the present examples. These data support the efficient transport of the APN-targeted VHHs across the small intestinal epithelium.

Because APN sequences are known to exist in cells from various species, the endogenous gene may be modified to permit, or increase, expression of the APN polypeptide. Cells can be modified (e.g., by homologous recombination) to provide increased expression by replacing, in whole or in part, the naturally occurring APN promoter with all or part of a heterologous promoter, so that the cells express APN polypeptide at higher levels. The heterologous promoter is inserted in such a manner that it is operatively linked to endogenous APN encoding sequences. It is also contemplated that, in addition to heterologous promoter DNA, amplifiable marker DNA (e.g., ada, dhfr, and the multifunctional cad gene, which encodes for carbamyl phosphate synthase, aspartate transcarbamylase, and dihydroorotase) and/or intron DNA may be inserted along with the heterologous promoter DNA. If linked to the APN coding sequence, amplification of the marker DNA by standard selection methods results in co-amplification of the APN coding sequences in the cells.

Alternatively, APN expression may also be induced by treatment with compounds known to induce expression of APN in a cell, such as for example a treatment with basic fibroblast growth factor (bFGF) [15], or with bestatin [16].

In one embodiment, the ISVD or polypeptide of the invention, is said to be "cross-reactive" for two different antigens or antigenic determinants (such as e.g., APN from different species of mammal, such as e.g. human APN, pig APN, dog APN, cat APN, horse APN, bovine APN, rat APN, mouse APN, and/or rhesus APN) if it is specific for (as defined herein) these different antigens or antigenic determinants. It will be appreciated that an ISVD or polypeptide may be considered to be cross-reactive although the binding affinity for the two different antigens can differ, such as by a factor, 2, 5, 10, 50, 100 or even more, provided it is specific for (as defined herein) these different antigens or antigenic determinants.

competing with a polypeptide as described herein, such as represented by any one of SEQ ID NO:s 6, 7 or 8, wherein the polypeptide as described herein competes with or cross blocks the competitor, such as a polypeptide, for binding to APN, such as, for instance porcine APN, wherein the binding to APN of the competitor is reduced by at least 5%, such as 10%, 20%, 30%, 40%, 50% or even more, such as 80%, 90% or even 100% (i.e. virtually undetectable in a given assay) in the presence of a polypeptide of the invention, compared to the binding to APN of the competitor in the absence of the polypeptide of the invention. In particular, a reduction of at least 80%, and preferably at least 90%, as measured by any one of the assays provided herein, indicates a competitive binding. Competition and cross blocking may be determined by any means known in the art, such as, for instance, a competitive binding assay such as flow cytometry, Surface Plasmon Resonance, Bio-layer interferometry or competition ELISA. In an aspect the present invention relates to a polypeptide of the invention, wherein said polypeptide cross-blocks the binding to APN of at least one of the polypeptides represented by SEQ ID Nos: 6, 7 or 8.

Assay conditions are applied as generally known to the skilled person and/or as provided herein.

The terms "(cross)-blocking", "competitive binding", and "competing" are used interchangeably herein to mean the ability of an immunoglobulin, antibody, ISVD, polypeptide or other binding agent to interfere with the binding of other immunoglobulins, antibodies, ISVDs, polypeptides or binding agents to a given target. Methods for determining whether an immunoglobulin, antibody, immunoglobulin single variable domain, polypeptide or other binding agent directed against a target (cross)-blocks, competitively binds or is competitive as defined herein are described e.g. in Xiao-Chi Jia et al. [17] or Miller et al. [18] (incorporated by reference).

The invention has identified a family of VHHs capable of binding APN, inducing transport across the intestinal epithelium and inducing an immune response. Said family of single domain antibodies are characterised by the following complementarity determining regions (CDR1 to CDR3 respectively), provided in Table 2.

VHHs having such a high sequence identity, esp. in CDR3 (80% identity or more), recognize the same epitope and are expected to have the same functional characteristics.

TABLE 2

| Clone | CDR1 | SEQ ID NO | CDR2 | SEQ ID NO | CDR3 | SEQ ID NO |
|---|---|---|---|---|---|---|
| AA | | | | | | |
| 2L65 | GRTISNHAMG | 1 | AISWTGLTTN | 3 | RQSGYVSKFVDDYGY | 4 |
| 3L2 | GRTISNHAMG | 1 | AISWTGLTTN | 3 | RQSGYVSKFVDDYGY | 4 |
| 3L73 | GRTFSSNAMG | 2 | AISWTGLTTN | 3 | RQSGYASKFLDEYGY | 5 |

In a further embodiment, the present invention relates to a polypeptide wherein said polypeptide competes with a polypeptide as described herein, such as represented by SEQ ID NO:s 6, 7 or 8, for instance as determined by a competitive binding assay such as flow cytometry, Surface Plasmon Resonance or competition ELISA, in particular by competition ELISA.

The invention further relates to a method for determining competitors, such as e.g. polypeptides or small molecules, In one embodiment, the invention provides a polypeptide comprising an immunoglobulin single variable domain (ISVD) binding intestinal aminopeptidase N, wherein said ISVD comprises 3 complementarity determining regions (CDR1 to CDR3, respectively), in which (i) CDR1 consists of an amino acid sequence represented by SEQ IN NO: 1, or a sequence having at least 70% identity thereto;

(ii) CDR2 consists of an amino acid sequence represented by SEQ IN NO: 3, or a sequence having at least 80% identity thereto;

(iii) CDR3 consists of an amino acid sequence represented by SEQ IN NO: 4, or a sequence having at least 80% identity thereto.

In another embodiment, the invention provides a polypeptide comprising an immunoglobulin single variable domain (ISVD) binding intestinal aminopeptidase N, wherein said ISVD comprises 3 complementarity determining regions (CDR1 to CDR3 respectively), in which (i) CDR1 is chosen from the group consisting of SEQ ID NOs: 1, and amino acid sequences that have 1, 2 or 3 amino acid difference(s) with SEQ ID NO: 1;

(ii) CDR2 is chosen from the group consisting of SEQ ID NOs: 3, and amino acid sequences that have 1, 2, or 3 amino acid difference(s) with SEQ ID NO: 3; and (iii) CDR3 is chosen from the group consisting of SEQ ID NO: SEQ ID NOs: 4, and amino acid sequences that have 1, 2, or 3 amino acid difference(s) with SEQ ID NO: 4.

In one embodiment, variant amino acids are at position(s) 4, 6 and/or 7 of the amino acid sequence represented by SEQ ID NO: 1; and/or at position(s) 6, 10 and/or 12 of the amino acid sequence represented by SEQ ID NO: 4.

In particular, the present invention relates to an ISVD as described herein, wherein said ISVD specifically binds APN and essentially consists of 4 framework regions (FR1 to FR4, respectively) and 3 complementarity determining regions (CDR1 to CDR3 respectively), in which (i) CDR1 is chosen from the group consisting of:

SEQ ID NO: 1; and an amino acid sequence that has 1, 2 or 3 amino acids difference with SEQ ID NO: 1, wherein at position 4 the I has been changed into F, and/or wherein at position 6 the N has changed to S, and/or wherein at position 7 the H has changed to N;

(ii) CDR2 consists of SEQ ID NO: 3; and (iii) CDR3 is chosen from the group consisting of:

SEQ ID NO: 4; and an amino acid sequence that has 1, 2 or 3 amino acids difference with SEQ ID NO: 4, wherein at position 6 the V has been changed into A, and/or wherein at position 10 the V has changed to L, and/or wherein at position 12 the D has changed to E.

In particular, the invention provides a polypeptide comprising an immunoglobulin single variable domain (ISVD), wherein said ISVD comprises 3 complementarity determining regions (CDR1 to CDR3 respectively), in which (i) CDR1 consists of SEQ ID NOs: 1 or 2;

(ii) CDR2 consists of SEQ ID NOs: 3; and (iii) CDR3 consists of SEQ ID NO: 4 or 5.

Even more particular, the invention provides a polypeptide comprising an immunoglobulin single variable domain (ISVD), wherein said ISVD comprises a CDR1, CDR2 and CDR3 combination that is chosen from:

CDR1 is SEQ ID NO: 1, CDR2 is SEQ ID NO: 3, and CDR3 is SEQ ID NO: 4; or

CDR1 is SEQ ID NO: 2, CDR2 is SEQ ID NO: 3, and CDR3 is SEQ ID NO: 5.

In a further embodiment, the invention provides a polypeptide comprising at least one immunoglobulin single variable domain (ISVD), said polypeptide comprising or consisting of the sequence of SEQ ID NO: 6, SEQ ID NO: 7, SEQ ID NO: 8, or a sequence having at least 80% identity thereto, in particular at least 85% identity, more in particular at least 90% identity, even more in particular at least 92% identity. In a particular embodiment, the sequence variation in the CDR is limited to position(s) 4, 6 and/or 7 of the amino acid sequence represented by SEQ ID NO: 1; and/or at position(s) 6, 10 and/or 12 of the amino acid sequence represented by SEQ ID NO: 4. In another embodiment, there is no sequence variation in the CDR as characterised by SEQ ID Nos: 1-5 resp., and only the sequence of the FR can differ. More specific, the invention provides a polypeptide comprising SEQ ID NO: 6, or a polypeptide which has at least 80%, more particular at least 85%, 86%, 87%, 88%, 89%, 90%, 91%, 92%, 93%, 94%, 95%, 96%, 97%, 98% or 99%, sequence identity to SEQ ID NO: 6 and wherein CDR1 consists of SEQ ID NOs: 1 or 2; CDR2 consists of SEQ ID NOs: 3; and/or CDR3 consists of SEQ ID NO: 4 or 5.

In another embodiment, the invention provides a polypeptide comprising at least one immunoglobulin single variable domain (ISVD), said polypeptide encoded by the nucleic acid sequence of SEQ ID NO: 10, SEQ ID NO: 11, SEQ ID NO: 12, or a sequence having at least 70% identity thereto, in particular at least 80% identity, more in particular at least 85% identity. In a particular embodiment, the sequence variation in the CDR is limited to position(s) 4, 6 and/or 7 of the encoded amino acid sequence represented by SEQ ID NO: 1; and/or at position(s) 6, 10 and/or 12 of the amino acid sequence represented by SEQ ID NO: 4. In another embodiment, there is no sequence variation in the CDR encoding the amino acids as characterised by SEQ ID Nos: 1-5 resp., and only the nucleic acid sequence of the FR can differ. More specific, the invention provides a polypeptide comprising at least one immunoglobulin single variable domain (ISVD), said polypeptide comprising or consisting of the sequence of SEQ ID NO: 6, SEQ ID NO: 7, or SEQ ID NO: 8.

It will be appreciated that, without limitation, the immunoglobulin single variable domains of the present invention may be used as a "building block" for the preparation of a polypeptide, which may optionally contain one or more further immunoglobulin single variable domains that can serve as a building block (i.e., against the same or another epitope on APN and/or against one or more other antigens, proteins or targets than APN). Hence, the polypeptide of the invention comprises at least one ISVD binding an APN, in particular binding an APN as well as being endocytosed by an APN expressing cell.

Generally, polypeptides or constructs that comprise or essentially consist of a single building block, e.g. a single ISVD, will be referred to herein as "monovalent" polypeptides and "monovalent constructs", respectively. Polypeptides or constructs that comprise two or more building blocks (such as e.g., ISVDs) will also be referred to herein as "multivalent" polypeptides or constructs, and the building blocks/ISVDs present in such polypeptides or constructs will also be referred to herein as being in a "multivalent format". For example, a "bivalent" polypeptide may comprise two ISVDs, optionally linked via a linker sequence, whereas a "trivalent" polypeptide may comprise three ISVDs, optionally linked via two linker sequences; etc.

Accordingly, the ISVDs of the invention that bind APN and provided herein can be in essentially isolated form, or they may form part of a construct or polypeptide, which may comprise or essentially consist of one or more ISVD(s) of the invention and which may optionally further comprise one or more further amino acid sequences (all optionally linked via one or more suitable linkers), encoding e.g. a protein or polypeptide, in particular an antigenic protein or polypeptide.

In a further embodiment, the present invention provides a "chimeric molecule" (optionally also referred to as a construct) comprising at least one polypeptide as defined herein, in particular at least one ISVD as provided herein, coupled, linked or conjugated (directly or indirectly) to at least one compound having a biological or functional activity, such as a chemical (e.g. small molecules) or biological, in particular a drug/therapeutic, a bio-active compound, an antigen, a toxin, and/or a diagnostic (e.g. a label, marker or imaging agent). In said embodiment, the polypeptide or ISVD will act as a carrier for the delivery of said compound across the intestinal barrier. The drug or therapeutic will be active in the intestinal submucosa or in the intestinal mucosa-associated lymphoid tissue and/or the antigen will induce an immune response in the intestinal submucosa or in the intestinal mucosa-associated lymphoid tissue. Said therapeutic agent may be an anti-inflammatory, anticancer, cytotoxic, anti-infective (e.g., anti-fungal, antibacterial, anti-parasitic, anti-viral, a toxin, a cytotoxic drug, a radionuclide, etc.) agent. Antigens include, but are not limited to proteins, peptides, lipids, nucleic acids, glycolipids and glycoproteins, carbohydrates, oligosaccharides, and polysaccharides. Also different drug delivery systems or (drug-loaded) carriers e.g. based on nanoparticles (NPs) can be conjugated to the polypeptide of the invention, including inorganic, magnetic, and polymeric particles or NPs.

The term "conjugated to", as used herein, refers, in particular, to chemical and/or enzymatic conjugation resulting in a stable covalent link. Coupling to obtain the chimeric molecule can occur via a specific amino acid (e.g. lysine, cysteine) present in the ISVD. As already mentioned, any moiety can be coupled, such as agents (e.g. proteins, nucleotide sequences, lipids, carbohydrates, peptides, drug moieties (e.g. cytotoxic drugs, antibody drug-conjugates or payload), tracers and detection agents) with a particular biological or specific functional activity. In the embodiment where the coupled moiety is a genetically encoded therapeutic or diagnostic protein or nucleotide sequence, the coupled moiety may be synthesized or expressed by either peptide synthesis or recombinant DNA methods that are well known in the art. In another aspect, where the conjugated moiety is a non-genetically encoded peptide, e.g. a drug moiety, the conjugated moiety may be synthesized artificially or purified from a natural source.

In a further embodiment, the polypeptide or the chimeric molecule as provided herein can further comprise one or more other groups, residues, moieties or binding units. The one or more other groups, residues, moieties or binding units are preferably chosen from the group consisting of a polyethylene glycol molecule, serum proteins or fragments thereof, binding units that can bind to serum proteins, an Fc portion or small proteins or peptides that can bind to serum proteins, further amino acid residues, tags or other functional moieties, e.g., toxins, labels, radiochemicals, etc. The other groups, residues, moieties or binding units may for example be chemical groups, residues, moieties, which may or may not by themselves be biologically and/or pharmacologically active. For example, and without limitation, such groups may be linked to the one or more ISVDs or polypeptides of the invention so as to provide a "derivative" of the polypeptide or construct of the invention.

In general, various linkers known in the art can be used to link the ISVD and the (bio-active) compound, agent or moiety according to the invention. As should be clear, cleavable and non-cleavable linkers can be employed to achieve the desired release profile. In general, the optimal combination of linker and conjugation chemistry must be uniquely tailored to correlate each unique facet: the ISVD, the conjugated moiety, and the profile of the disease to be treated. Still other suitable spacers or linkers will be clear to the skilled person, and may generally be any linker or spacer used in the art. In specific aspects the linkers or spacers are suitable for use in applications which are intended for pharmaceutical use. For example, a linker between the lysine and the conjugate may in certain aspects also be a suitable amino acid sequence, and in particular amino acid sequences of between 1 and 50, or more specifically, between 1 and 30 amino acid residues. Some examples of such amino acid sequences include Gly-Ser (GS) linkers. Still other suitable linkers generally comprise organic compounds or polymers, in particular those suitable for use in polypeptides for pharmaceutical use. For instance, poly(ethyleneglycol) moieties have been used to link antibody domains. It is encompassed within the scope of the invention that the length, the degree of flexibility and/or other properties of the linker may have some influence on the properties of the final ISVD conjugate of the invention, including but not limited to the affinity, specificity or avidity for a specific target. Based on the disclosure herein, the skilled person will be able to determine the optimal linker for use in a specific ISVD of the invention, optionally after some limited routine experiments.

The small size and fast renal clearance of VHH are sometimes less favorable characteristics to provide long term protection in certain diseases. Several approaches ensure the prolongation of half-life and are considered embodiments of the present invention. Hence, the efficacy of the current VHHs can be improved by fine-tuning the residence time. The VHHs provided herein can be chemically modified in order to increase their molecular weight. Such a chemical modification, for example with a polyethylene glycol (PEG) group, may also protect the VHH against proteases. Another strategy to extend the half-life of a VHH is by coupling the VHHs to long-lived serum proteins or to building blocks that target these long-lived proteins. Furthermore, it has been observed that negatively charged small proteins remain longer in circulation than neutral proteins. There are several ways to add negative charges to proteins including the addition of sialic acid polymers (polysialylation) or hydroxyethal starch (HESylation) and by fusion with the highly sialyated beta carboxyterminal peptide (CTP) amino acid-residue found in the human chorionic gonadotropin (hCG) hormone. Finally, 'Fc domain-based fusion constructs' are also widely used to extend the half-life of therapeutic proteins, including VHHs. Hence a further strategy is to fuse the VHH of the invention to the Fc region or other Fc-moieties of an IgG molecule. However, other Fc domains are also qualified, such as the Fc domain of IgA which is more stable in the small intestinal environment.

For example, in order to increase affinity and avidity and at the same time allow easy purification, the VHH domains of the present invention are fused to the Fc domain of mouse IgG, more specifically mouse IgG2a, also referred to herein as VHH-MG fusions. VHHs of the present invention fused to the Fc domain of pig IgG or pig IgA are also part of the present invention and are referred to herein as VHH-PG or VHH-PA fusions respectively. Suitable Fc domains or parts thereof are e.g. provided in FIG. 10.

In one embodiment, the present invention provides a chimeric molecule comprising at least one polypeptide, in particular an ISVD, as provided herein, and an Fc region or Fc binding moiety, in particular an IgG or IgA Fc domain, such as e.g. an Fc domain comprising or consisting of either one of SEQ ID NO: 18-21. In a specific embodiment, the invention provides a polypeptide comprising an ISVD comprising SEQ ID NO:6, SEQ ID NO:7 or SEQ ID NO:8; fused to an Fc domain comprising or consisting of SEQ ID NO: 18, SEQ ID NO: 19, SEQ ID NO: 20, or SEQ ID NO: 21, or a part thereof or a sequence having at least 80%, at least 85%, or at least 90% identity thereto.

The polypeptide of the present invention, in particular the immunoglobulin single variable domains as described herein, in their broadest sense are not limited to a specific biological source or to a specific method of preparation. They can generally be obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "mutation" of a naturally occurring VHH domain to reduce binding to pre-existing antibodies, or by expression of a nucleic acid encoding such a mutated VHH domain; (5) by "camelization" of a naturally occurring VH domain from any animal species, and in particular from a mammalian species, such as from a human being, or by expression of a nucleic acid encoding such a camelized VH domain; (6) by "camelization" of a "domain antibody" or "Dab" as described in the art, or by expression of a nucleic acid encoding such a camelized VH domain; (7) by using synthetic or semisynthetic techniques for preparing proteins, polypeptides or other amino acid sequences known per se; (8) by preparing a nucleic acid encoding a Nanobody® using techniques for nucleic acid synthesis known per se, followed by expression of the nucleic acid thus obtained; and/or (9) by any combination of one or more of the foregoing. An ISVD is "camelized" by replacing one or more amino acid residues in the amino acid sequence of a naturally occurring V domain from a conventional 4-chain antibody by one or more of the amino acid residues that occur at the corresponding position(s) in a VHF domain of a heavy chain antibody. This can be performed by any method known to the skilled person. Such "camelizing" substitutions are preferably inserted at amino acid positions that form and/or are present at the VH-VL interface, and/or at the so-called Camelidae hallmark residues, well known to the person skilled in the art and which have been defined for example in WO 94/04678 and Davies and Riechmann [19].

Furthermore and as is known to the skilled person, different production platforms such as mammalian cells, yeast, plants, etc. can be used for the production of complex assembled glycoproteins such as antibodies. Production based on mammalian cells, like Chinese Hamster Ovary (CHO) cells is straightforward for the production of antibodies. Transgenic plants and yeast expression systems also show a great potential. Yeast, such as Komagataella phaffii [20], which was previously named and better known under the old nomenclature as *Pichia pastoris*, possesses a clear advantage over plant expression systems in terms of short generation time, cost effectiveness, ease of genetic manipulation and scalability. Moreover, *P. pastoris* secretes very low amounts of endogenous proteins, therefore secreted recombinant proteins are highly enriched, which facilitates downstream processing. On the other hand, the glycosylation profile of recombinant proteins in plants is much more alike that of animal cells than the yeast expression platform.

In one embodiment, the present invention provides the production of the polypeptide, in particular the ISVD, even more particular the chimeric molecule, as provided herein using a yeast, in particular *Pichia pastoris*.

The multivalent polypeptides or chimeric molecules of the invention can generally be prepared by a method which comprises at least the step of suitably linking the ISVD and/or monovalent polypeptide of the invention to one or more further ISVDs, or other compounds as described herein, optionally via one or more suitable linkers, so as to provide the polypeptide or chimeric molecule of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

In a further embodiment, the invention relates to a vector comprising the nucleotide sequence as provided herein. The term "vector", as used herein, includes any vector known to the skilled person, including plasmid vectors, cosmid vectors, phage vectors, such as lambda phage, viral vectors, such as adenoviral, AAV or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Typically, an "expression vector" comprises a nucleotide sequence in which an expressible promoter or regulatory nucleotide sequence is operatively linked to, or associated with, a nucleotide sequence or DNA region that codes for an mRNA, such that the regulatory nucleotide sequence is able to regulate transcription or expression of the associated nucleotide sequence. Typically, a regulatory nucleotide sequence or promoter of the vector is not operatively linked to the associated nucleotide sequence as found in nature, hence is heterologous to the coding sequence of the DNA region operably linked to.

Another embodiment relates to a host cell or expression host comprising the polypeptide, or the chimeric molecule, or the nucleic acid sequence provided by the present invention. The term "host cell", "expression host", or "host" refers to the cellular system used to express the protein or nucleic acid of interest, in a recombinant manner (formed by genetic recombination). A host cell can relate to a "higher eukaryotic cell" (e.g. a CHO cell line), typically being part of a cell culture (e.g. a cell line, such as a HEK or CHO cell line), although this is not always strictly required (e.g. in case of plant cells, the plant itself can be used to produce a recombinant protein). A host cell can also relate to a "lower eukaryotic cell" as used herein where a filamentous fungus cell or a yeast cell is meant. Yeast cells can be from the species *Saccharomyces* (e.g. *Saccharomyces cerevisiae*), *Hansenula* (e.g. *Hansenula polymorpha*), *Arxula* (e.g. *Arxula adeninivorans*), *Yarrowia* (e.g. *Yarrowia lipolytica*), *Kluyveromyces* (e.g. *Kluyveromyces lactis*), or Komagataella phaffii (*Pichia pastoris*), and can also further be used herein. According to a specific embodiment, the lower eukaryotic cells are *Pichia* cells, and in a most particular embodiment *Pichia pastoris* cells. Host cells relating to "prokaryotic cells" typically refer to non-pathogenic prokaryotes like bacterial cells such as for example *E. coli, Lactococcus* and *Bacillus* species.

In a further embodiment, the current invention provides the ISVD, the polypeptide, chimeric molecule, the nucleic acid, the vector, the host cell or composition provided herein for use as a medicament, more in particular for use in preventing, treating and/or reducing symptoms of an intestinal disease, even more in particular for use in oral vaccination against intestinal disease. 'Intestinal disease' as used herein refers to gut or enteric infections and inflammatory disease of the gut or intestines, more specific the small intestines (e.g. Inflammatory bowel disease, Crohn's disease or ulcerative colitis). Such Inflammation can e.g. be caused by an autoimmune disease. Infections with intestinal pathogens includes infection with a species selected from the group of genera consisting of: pathogenic *Escherichia coli* (ETEC, EHEC, EPEC, STEC, . . . ), *Vibrio, Campylobacter, Clostridium, Salmonella, Yersinia, Lawsonia, Rotavirus, Shigella*, PEDV, *Cryptosporidium*, and *Isospora*. In particular, the invention provides a method for treating and/or preventing an intestinal disease by administering a polypeptide, chimeric molecule or composition of the invention to a subject. In one embodiment, administration is orally. The IVSD as provided herein can function as a carrier, targeting a compound, in particular a bio-active compound, more in particular an antigen, across the (gastro)intestinal mucosa. In one aspect, the present invention focuses on the polypeptide or ISVD as a carrier for targeted vaccine delivery to the gut epithelium to induce strong mucosal immune responses, e.g. against gut pathogens. As used herein, "mucosal immune response" refers to an immune response (humoral and cellular response) that occurs at a mucosal membrane of the intestine, the urogenital tract and/or the respiratory system, i.e., surfaces that are in contact with the external environment. In the context of the present invention, the mucosal immune response is an intestinal mucosal immune response occurring at a mucosal membrane of the small intestine, in particular the production of immunoglobulin A (IgA). The invention furthermore provides a method for treating an intestinal disease and/or to induce an immune response against an intestinal pathogen in a subject by orally administering the ISVD, a polypeptide, chimeric molecule or composition as provided herein to the subject.

In another embodiment, the invention relates to the use of an ISVD, polypeptide and/or chimeric molecule of the invention in the preparation of a pharmaceutical composition. Hence, also provided is a pharmaceutical composition and its use in one or more of the methods of treatment mentioned herein. Typically, the pharmaceutical composition comprises the ISVD, polypeptide and/or construct as described herein and a pharmaceutically acceptable carrier and/or excipient, optionally in combination with an adjuvant.

A "carrier", or "adjuvant", in particular a "pharmaceutically acceptable carrier" or "pharmaceutically acceptable adjuvant" is any suitable excipient, diluent, carrier and/or adjuvant which, by themselves, do not induce the production of antibodies harmful to the individual receiving the composition nor do they elicit protection. By "pharmaceutically acceptable" is meant a material that is not biologically or otherwise undesirable, i.e., the material may be administered to an individual along with the compound without causing any undesirable biological effects or interacting in a deleterious manner with any of the other components of the pharmaceutical composition in which it is contained. A pharmaceutically acceptable carrier is preferably a carrier that is relatively non-toxic and safe to a patient at concentrations consistent with effective activity of the active ingredient so that any side effects ascribable to the carrier do not impair the beneficial effects of the active ingredient. Preferably, a pharmaceutically acceptable carrier or adjuvant enhances the immune response elicited by an antigen. Suitable carriers or adjuvantia typically comprise one or more of the compounds included in the following non-exhaustive list: large slowly metabolized macromolecules such as proteins, polysaccharides, polylactic acids, polyglycolic acids, polymeric amino acids, amino acid copolymers and inactive virus particles. The term "excipient", as used herein, is intended to include all substances which may be present in a pharmaceutical composition and which are not active ingredients, such as salts, binders (e.g., lactose, dextrose, sucrose, trehalose, sorbitol, mannitol), lubricants, thickeners, surface active agents, preservatives, emulsifiers, buffer substances, stabilizing agents, flavouring agents or colorants. A "diluent", in particular a "pharmaceutically acceptable vehicle", includes vehicles such as water, saline, physiological salt solutions, glycerol, ethanol, etc. Auxiliary substances such as wetting or emulsifying agents, pH buffering substances, preservatives may be included in such vehicles.

The polypeptides, and chimeric molecules of the invention and optionally a pharmaceutically acceptable carrier and/or excipient can be administered by any suitable route such as any of those commonly known to those of ordinary skill in the art. For therapy, the pharmaceutical composition of the invention can be administered to any patient in accordance with standard techniques. The administration can be by any appropriate mode, including orally, parenterally, topically, nasally, ophthalmically, intrathecally, intraventricularly, sublingually, rectally, vaginally, and the like, and preferably orally. Still other techniques of formulation as nanotechnology and aerosol and inhalant are also within the scope of this invention. The dosage and frequency of administration will depend on the age, sex and condition of the patient, concurrent administration of other drugs, counter-indications and other parameters to be taken into account by the clinician. The dosage and concentration of the carrier, excipient and stabilizer should be safe to the subject (human, pigs, mice and other mammals), including buffers such as phosphate, citrate, and other organic acid; antioxidant such as vitamin C, small polypeptide, protein such as serum albumin, gelatin or immunoglobulin; hydrophilic polymer such as PVP, amino acid such as amino acetate, glutamate, asparagine, arginine, lysine; glycose, disaccharide, and other carbohydrate such as glucose, mannose or dextrin, chelate agent such as EDTA, sugar alcohols such as mannitol, sorbitol; counterions such as Na+, and/or surfactant such as TWEEN®, PLURONICS® or PEG and the like.

A further aspect of the invention relates to a method to produce the APN binding polypeptide of the invention comprising the steps of expression of the polypeptide or chimeric molecule as provided herein, in a suitable expression system or host cell, in particular in *Pichia pastoris*, and purification or isolation of said APN binding polypeptide.

With purification or isolation of said expressed polypeptide is for instance meant, without limitation, affinity-based purification such as affinity chromatography, affinity purification, immunoprecipitation, protein detection, immunochemistry, surface-display, amongst others, and all well-known in the art.

Yet another aspect of the invention relates to a kit comprising a polypeptide, chimeric molecule or nucleic acid according to the invention. The kit may further comprise a combination of reagents such as buffers, molecular tags, vector constructs, reference sample material, as well as a suitable solid support, cells, nucleic acids, and the like. Such a kit may be useful for any of the applications of the present invention as described herein. Also encompassed within the scope of the present invention is a solid support or resin comprising a polypeptide comprising an APN binding ISVD according to the present invention. Non-limiting examples of suitable solid supports include beads, columns, slides, chips or plates. More specifically, the solid supports may be particulate (e.g. beads or granules, generally used in extraction columns) or in sheet form (e.g. membranes or filters, glass or plastic slides, microtiter assay plates, dipstick, capillary fill devices or such like) which can be flat, pleated, or hollow fibers or tubes. Immobilization may be either non-covalent or covalent, using techniques known in the art.

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

EXAMPLES

Materials and Methods

1. Vectors, Strains, and Cell Lines

For the VHH library preparation, the pMECS phage display vector system was used that contains the pelB signal sequence to secrete the expressed VHH in bacterial periplasm and that adds an HA and His6 tag at the VHH carboxy-terminal end, enabling purification. The yeast expression vector pPICZalphaH6E (NCBI accession number KM035419.1) modified for GoldenBraid cloning (named pKaiGG) was used for cloning the VHH-MG (MG: Fc domain of murine IgG) fusions under the control of the methanol-inducible AOX1 promoter. The vector contains the Zeocin resistance marker for selection in bacterial as well as yeast cells. *E. coli* strains TG1 and DH5a were used for construction of the VHH library and fusion expression vectors, respectively. The VHH-MG fusions were expressed in the *P. pastoris* wild-type strain NRRL Y-11430 (ATCC 76273). Stable APN-expressing cell lines (intestinal porcine epithelial cells IPEC-J2 and baby hamster kidney BHK-21) were obtained by transfection and cultured as previously described [3, 4].

2. Purification of Intestinal APN

Enterocytes were isolated from the small intestine of a 3-week-old piglet following the method of Lundqvist, Hammarström, Athlin and Hammarström [21]. After analysis using light microscopy, more than 85% enterocyte purity was observed. Next, brush border membrane vesicles (BBMVs) were isolated from the enterocytes as described by Melkebeek, Rasschaert, Bellot, Tilleman, Favoreel, Deforce, De Geest, Goddeeris and Cox [3]. The obtained BBMVs were subsequently lysed in 9 volumes of lysis buffer (100 mM Tris-HCl, 300 mM NaCl, 1% Triton X-100, 0.5% sodium deoxycholate, 0.1% SDS, 2 mM leupeptin, 5 mM DTT, 1 mM AEBSF), sonicated for 2 min on ice, rotated for 30 min at 4° C. and centrifuged at 17,400 g for 15 min at 4° C. Supernatant was collected and dialyzed in PBS using a 10 kDa MWCO dialysis cassette (Thermo scientific). Protein concentration was determined by BCA reaction (Pierce BCA protein assay kit), following the manufacturer's recommendations. Lysates were stored at −20° C. until further use.

Intestinal pAPN was purified by immunoprecipitation from these lysates. First, affinity-purified rabbit anti-APN IgG (in house) was crosslinked to protein A Sepharose beads (CL-4B, Sigma). For this, 50 mg of beads were washed three times in 1 ml distilled water to remove salts by centrifugation at 400 g for 2 min. Rabbit anti-APN IgG (4 mg) was added to the beads for 1 h in PBS at room temperature (RT). Next, beads were washed twice with 1 ml 0.2 M sodium borate buffer (pH 8.0), after which 1 ml 0.2 M sodium borate (pH 9.0)+20 mM dimethylpimelimidate (DMP, Sigma) was added for 30 min at RT. After crosslinking, the beads were washed twice for 1 h in 1 ml 0.2 M ethanolamine+50 mM ammonium bicarbonate buffer (pH 8.0). Next, the beads were washed thrice in PBS before elution buffer (0.2 M Glycine-HCl, 50 mM L-arginine, 1 M NaCl (pH 2.0)) was added to remove non-crosslinked IgGs. Beads were washed again three times in PBS and stored at 4° C. until further use. Finally, the anti-APN-beads were incubated with 1 ml of BBMV lysate overnight at 4° C. on a rotating wheel. Beads were centrifuged (400 g, 2 min, 4° C.) and supernatant was collected. Beads were washed thrice with PBS to remove unbound proteins. Next, APN was eluted from the beads with elution buffer for 10 min at RT. After centrifugation, supernatant was collected and neutralized with 1 M Tris-HCl (pH 9.0). Eluted APN was dialyzed immediately in PBS and stored at −20° C. Concentration was determined with the Pierce BCA protein assay kit and purity (>95%) was assessed by performing a silver staining (Pierce® silver stain kit; Thermo Scientific), following the manufacturer's instructions.

3. Generation of a pAPN-Specific VHH Library

Porcine APN-specific VHHs were developed by the VIB Nanobody Core facility, Brussels (Belgium), as described previously [22]. Briefly, two llamas were immunized subcutaneously on days 0, 7, 14, 21 and 28, each time with 320 μg (per animal) APN isolated from porcine kidney (Sigma, cat. No. L6007-50UN). On day 35, each llama received a final booster with 200 μg of APN isolated from pig intestine. The porcine intestinal APN was purified as described above. For all immunizations, Gerbu P (GERBU Biotechnik) was used as adjuvant. On day 40, anticoagulated blood was collected for lymphocyte preparation. Total RNA from peripheral blood lymphocytes (PBLs) was used as template for first strand cDNA synthesis with an oligo(dT) primer. Using this cDNA, the VHH-encoding sequences were amplified by PCR, digested with PstI and NotI, and cloned into the PstI and NotI sites of the phagemid vector pMECS, and in this way fused to a histidine tag. Electrocompetent *E. coli* TG1 cells were transformed with the recombinant pMECS vector. An independent VHH library was obtained from each of the llamas, and each was subjected to a panning (in solution), performed on stably transfected BHK-21 cells expressing pAPN. The phage outputs of the first panning round from the two libraries were then pooled and the pool was used for further panning rounds. 190 randomly selected colonies from the second and third panning rounds (95 from each round) were sequenced and then grouped based on their CDR3 sequences. Using crude periplasmic extracts, 28 unique VHH (Nanobody®) sequences were analyzed by flow cytometry for specificity to pAPN using pAPN-expressing BHK-21 cells.

4. Construction of the VHH-MG Fusion Expression Vectors

To clone the in silico designed VHH-MG fusions in the yeast expression vector pKaiGG, customized reagents designed for Gibson Assembly® cloning were obtained from SGI-DNA (La Jolla, California), being synthetically produced DNA fragments of the VHH-encoding sequences fused to the Fc tail of mouse IgG2a (Hinge-CH2-CH3; NCBI accession number KC295246.1) with 40-base overlaps between the insert and the vector. The expression vector pKaiGG adapted for Golden Gate cloning was digested with SapI and column purified (GeneJET PCR purification kit, ThermoFisher Cat. No. K0701). The VHH fragments were always assembled with the same Fc fragment and were cloned at the 5' end inframe with the alpha factor secretion signal sequence (from novel *P. pastoris* expression vector named pPICZH6E; GenBank accession number KM035419) and at the 3' end with the transcription termination sequence into the in-house SapI-digested pKaiGG vector via the BioXp™ 3200 System in an approximately 18 h reaction and transformed into *E. coli* DH5a. Upon plasmid preparation and sequence confirmation of the insert, yeast cells were transformed with the PmeI-linearized vectors and positive transformants were selected on YPD (1% yeast extract, 2% peptone, 2% Dextrose) supplemented with 50 mg/ml Zeocin (Invitrogen).

5. Production of VHH-MG Fusions in *P. pastoris*

Expression and secretion of the VHH-MG fusions in the medium was first analyzed in 2 ml cultures. On day one, 2 ml of BMGY medium (1% Bacto yeast extract, 2% peptone, 1.34% YNB, 0.1 M potassium phosphate (pH 6), 1% glycerol) with 25 mg/ml Zeocin was inoculated with individual transformants and incubated while shaking at 28° C. for 48 h. For each VHH-MG construct, four independent transformants were grown in 24-well plates. The cells were then pelleted for 10 min at 1500 g and resuspended in 2 ml BMMY medium (1% Bacto yeast extract, 2% peptone, 1.34% YNB, 0.1 M potassium phosphate (pH 6), 1% methanol) to induce expression of VHH-MG. Cultures were incubated while shaking at 28° C. for 48 h and spiked with 1% methanol (v/v) every 12 h. After 48 h of induction, the yeast cells were pelleted, and the supernatant was analyzed by SDS-PAGE, western blot and ELISA to assess the accumulation levels of the secreted VHH-MG fusions in the medium.

6. Affinity Purification of VHH-MG Fusions

Yeast transformants that yielded high levels of VHH-MG were selected for upscaling in 11 cultures, using similar growth and induction conditions as described above for 2 ml cultures. *P. pastoris* cultures grown in baffled flasks were harvested after 48 h of induction. Culture supernatant was filtered using 0.22 μM PES membrane filters (Millipore) and affinity purified on a 1 ml HiTrap MabSelect SuRe protein A column (GE healthcare), equilibrated with 20 mM sodium phosphate, 300 mM NaCl buffer, pH 7.8. Bound protein was eluted with 1 M arginine, pH 2.7 and immediately neutralized with 1 M Tris, pH 9. Relevant fractions with high concentration of VHH-MG were pooled and subjected to size-exclusion chromatography (Superdex 200, GE Healthcare). Fractions containing the major antibody peak in the chromatogram were pooled, concentrated by dialyzing against 20% polyethylene glycol in PBS and stored at −80° C. until use. The protein concentration was determined by OD280 measurement.

7. SDS-PAGE and Western Blotting

VHH-MG fusions (crude/purified) were analyzed on a commercial 4 to 20% gradient gel (Bio-Rad) under reducing conditions and stained with Coomassie G-250 following the manufacturer's instructions. For western blotting, proteins were transferred onto a polyvinylidene difluoride membrane (PVDF) using the semidry transfer method (Bio-Rad). Blotted membrane was blocked overnight with 2% skimmed milk in PBST (PBS+0.1% (v/v) Tween-20) at 4° C. Thereafter, the membrane was probed with anti-mouse IgG (GE Healthcare, NXA931) conjugated to horseradish peroxidase (HRP), diluted 1:2000 in blocking solution and incubated for 1 h at RT. The membrane was then washed three times with PBST, and bands were visualized by adding HRP substrate (WesternBright ECL, Advansta). The membrane was imaged using a ChemiDoc MP imaging system (Bio-Rad) and analyzed by ImageLab software (Bio-Rad).

8. Antigen-Binding ELISA 96-well ELISA plates (Nunc Polysorp®) were coated for two h at 37° C. with 400 ng of APN (Sigma) diluted in PBS. Plates were then washed three times with PBST and blocked overnight at 4° C. with 3% (w/v) gelatin prepared in PBS and 0.05% Tween-80. Following three washes with PBST, VHH-MG fusions were serially diluted in dilution buffer (2% skimmed milk+PBS+0.05% Tween-20), added to each well and incubated for 1 h at RT. An in-house produced pAPN-specific mAb (IMM013, see ref. [4]) was used as a positive control, while a GFP-specific VHH fused to a murine IgG3 (GBP-MG) was used as a negative control [23]. After washing, bound VHH-MG fusions were detected by anti-mouse IgG (GE Healthcare, NXA931), diluted 1:5000 in the dilution buffer. Following incubation for 1 h at RT, plates were washed three times with PBST and developed by adding HRP substrate (one SIGMAFAST™ OPD tablet dissolved in 20 ml deionized water). Finally, the reaction was stopped with 1 M hydrochloric acid and the optical density of the colorimetric reaction was measured at 492 nm (VersaMax™).

9. Flow Cytometry

Binding of the different VHH-MG fusions to APN-expressing cell lines was analyzed using flow cytometry. The wild-type and APN-transfected IPEC-J2 and BHK-21 cell lines were grown until reaching a 90% confluence and detached with StemPro accutase (Gibco). Detached cells ($3.0\times10^5$) were transferred to a conical bottom 96-well microtiter plate (Gibco) in 200 μl culture medium and centrifuged for 3 min at 350 g and 4° C. Cells were incubated with 2 μg/ml VHH-MG fusions or anti-APN mAb (clone IMM013) on ice for 30 min. Detection of bound VHH-MG fusions was performed with an AF647-conjugated anti-mouse IgG2a antibody (4 μg/ml; Invitrogen, A21241) and with an AF647-conjugated anti-mouse IgG1 antibody (4 μg/ml; Invitrogen, A-21240) for IMM013. Cells were incubated for 30 min on ice. Dead cells were excluded using Sytox blue staining (5 nM; Molecular probes). A total of 10,000 viable, single cells was measured for each condition (Cytoflex, Beckman Coulter).

10. VHH-MG Endocytosis Assay

APN-expressing BHK-21 cells were seeded in 24-well plates ($1.0\times10^5$ cells in 1 ml) on top of a sterile cover slip and cultured until a monolayer was formed. Cells were washed twice with ice-cold PBS and stored on ice before the VHH-MG fusions or IMM013 were added to the cells (250 μl; 100 μg/ml) in ice-cold culture medium. After a 30 or 60 min incubation at 4° C., cells were washed thrice with ice-cold PBS and incubated for 30 min at 37° C., 5% CO2 in warm culture medium. After washing twice in PBS, cells were fixed for 10 min at room temperature (RT) with 500 μl 4% paraformaldehyde. Next, the presence of VHH-MGs or IMM013 on the cell membrane was detected with an AF568-conjugated anti-mouse IgG (H+L) (2 μg/ml; Invitrogen, A-11004) for 30 min at RT and protected from light. After washing three times with PBS+1% FCS, cells were permeabilized with 250 μl 0.2% Triton-X100 for 2 min and washed again with PBS+1% FCS. Both VHH-MG and IMM013 were then detected using a FITC-conjugated anti-mouse IgG (1/50; whole molecule) (Sigma, F2883) for 30 min at RT, protected from light. Nuclei were visualized with Hoechst (1/100 dilution) staining. After washing three times, the cover slip was taken out and mounted on a microscope slide in mounting solution (antifading agent 1, 4-Diazobicyclo-2,2,2-octane-DABCO™). Images were taken with a confocal microscope (Leica).

11. In Vivo Uptake of Anti-APN VHH-MG

Three female, 5-week-old piglets were used to assess the uptake of the VHH-MGs in gut ligated loops as described previously [24]. Briefly, following anesthesia and laparotomy, the jejunum was localized and six 3 cm loops with 10 cm intervals between each loop were made avoiding Peyer's patches. Blood supply was assured by placing the ligatures between the mesenteric arcades. The pAPN-specific mAb (IMM013, see ref. [4]) was used as a positive control, while GBP-MG was used as a negative control [24]. The anti-APN mAb IMM013 (1 mg) or an equimolar amount of the different VHH-MGs were diluted in 3 ml of PBS and injected in the lumen of the loops. Upon injection, each loop was returned to the abdominal cavity and the abdomen was closed. After a 5 h incubation, the animals were euthanized with an overdose of sodium pentobarbital and tissue samples from intestines, loops and mesenteric lymph nodes were collected. Tissue samples were embedded in 2% Methocel® MC (Fluka), snap frozen in liquid nitrogen and stored at −80° C. until use. All animal procedures were approved by the Ethical Committee of the Faculty of Veterinary Medicine of Ghent University (EC 2018-04).

12. Immunohistochemistry

Cryosections (8 μm) of porcine ileum obtained from 3-week-old piglets or from the gut loops were cut with a Leica CM3050 S cryostat, mounted on APES-coated glass slides, dried (30 min, 40° C.) and fixed in acetone during 10 min at −20° C. Subsequently, the cryosections were incubated during 30 min in ammonium chloride buffer (50 mM, pH 8) and washed thoroughly. All washing steps were carried out at RT in PBS. Fc receptors were blocked for 30 min at 37° C. with PBS containing 10% sheep or goat serum. Binding of the VHH-MG or IMM013 was detected by incubation for 1 h at 37° C. with a FITC-conjugated sheep anti-mouse IgG (10 μg/ml; Sigma; F2883) or goat anti-mouse IgG2a. Nuclei were counterstained with Hoechst (10 μg/ml). To assess endocytosis sections were stained with a rabbit anti-pan-cytokeratin antibody (Abeam, ab9377) and detected with a TexasRed-conjugated anti-rabbit IgG. The sections were washed in ultrapure water and mounted in mounting solution (DABCO). Tissues were imaged with a Leica DC 100 fluorescence microscope mounted with a Scion Corporation camera or a Leica confocal microscope. Images were analyzed and processed using Fiji.

13. Oral Immunization Experiment

Figure 6A:
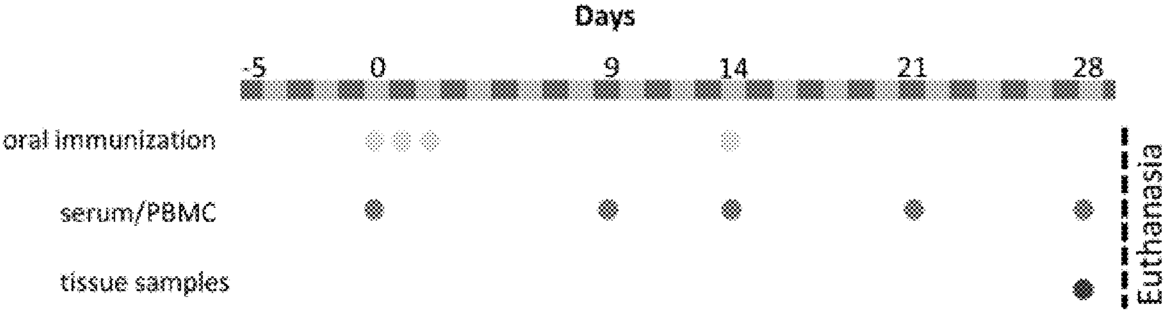
FIGS. 6A-6D: Oral immunization of piglets with VHH-MG triggers circulating and small intestinal antibody responses.

All animal procedures were approved by the ethical committee of the Faculty of Veterinary Medicine (EC 2018-51). Twelve conventionally reared piglets (Belgian Landrace x Pietrain) from a Belgian farm were weaned at 3 weeks of age and transported to our facilities. Animals were treated with colistin sulphate (Promycine®, 100.000 U.I./kg of animal weigh) for 5 days before the start of the experiment. The design of the oral immunization experiment is depicted in FIG. 6. Animals were randomly divided in three groups: a mouse IgG2a control group and two groups receiving either the APN-specific VHH-MGs 2L65 or 3L94. Animals were orally immunized on three consecutive days followed by a booster immunization on day 14 post primary immunization. The HCl production in the stomach was blocked by administering Omeprazole (20 mg/animal) 24 hours before each immunization and animals were deprived of feed 12 hours before the immunizations. The animals were orally immunized with either 1 mg of 3L94-MG, 2L65-MG or an equimolar amount of an irrelevant mouse IgG2a (Bio X cell; West Lebanon, USA), adjuvanted with 50 μg of cholera toxin (Merck, ref: C8052). Blood was collected on days 0, 9, 14, 21 and 28 post primary immunization (ppi) to analyze the elicited immune responses. At day 28 ppi animals were euthanized by intravenous injection of sodium pentobarbital 20% (60 mg/2.5 kg; Kela) and upon exsanguination small intestinal tissue samples were collected.

14. Mouse IgG2a ELISA

Blood was taken from the jugular vein into a gel and clot activator tubes (Vacutest, Kima). After 1 h incubation at room temperature, tubes were centrifuged, and serum was collected and inactivated at 56° C. during 30 min. Serum samples were stored at −20° C. until use.

An in-house produced mouse IgG2a monoclonal antibody was coated in 96-well microtiter plates (Polysorp; Life Technologies) at 6 μg/ml in PBS for 2 h at 37° C. Upon overnight blocking at 4° C. in PBS supplemented with 0.2% Tween80 and 3% BSA, diluted serum samples (start dilution 1:10 in dilution buffer) were added to the wells. Upon incubation for 1 hat 37° C., plates were washed and incubated for 1 h at 37° C. with HRP-conjugated mouse anti-swine IgG (MT424, 1/1000; MabTech, Nacka Strand, Sweden) or HRP-conjugated goat anti-swine IgA (1/10.000; Bethyl; Montgomery, Texas, U.S). Following three washing steps, 2,2'-azino-bis(3-ethylbenzothiazoline-6-sulphonic acid) (ABTS) substrate was added and the optical density was measured at 405 nm after 45 min incubation at 37° C. using a spectrophotometer (Tecan SpectraFluor).

15. ELIspot

Blood was taken on heparin from the jugular vein of piglets and PBMCs were isolated by density gradient centrifugation using Lymphoprep® (Alere Technologies, Oslo, Norway). Erythrocytes were lysed in ammonium chloride solution. The resulting PBMC fraction was washed twice in ice cold PBS+1 mM EDTA, resuspended in CTL-test BTM (Cellular Technology Limited, Cleveland, USA) supplemented with 1% penicillin (100 IU/mL), streptomycin (100 μg/mL) and kanamycin to 1×107 cells/ml. Mononuclear cells (MCs) were isolated from mesenteric lymph nodes (MLN), jejunal Peyer's Patches (JPP), jejunal lamina propria (JLP), ileal Peyer's Patches (IPP) and ileal lamina propria (ILP) and processed as described previously [25]. Isolated MC were resuspended in leukocyte medium (RPMI-1640 (Gibco) containing 10% fetal calf serum, 1 mM sodium pyruvate, 2 mM 1-glutamine, penicillin (100 IU/mL), streptomycin (100 μg/mL), and non-essential amino acids (1%) and counted.

MultiScreen filter plates (96-well format, MAIPA4510, Millipore) were activated with 70% ethanol, washed with ultrapure (UP) water and coated with 10 μg/ml mouse IgG2a overnight at 4° C. Upon washing, the plates were incubated for 2 h at 37° C. with CTL-test B medium. Mononuclear cells (2.5×105/well) from each tissue were added to the wells and incubated for 18 h at 37° C. in a humidified 5% CO2 atmosphere. Cells were then removed by intensive washing with PBS containing 0.1% Tween20. Upon washing, HRP-conjugated anti-swine IgG (MT424, 1/1000; MabTech) or IgA (1/10.000; Bethyl laboratories) was added in assay buffer (PBS containing 0.1% Tween20 and 0.1% BSA) and incubated for 1 hour at room temperature. Finally, 3,3',5,5'-Tetramethylbenzidine (TMB) substrate for membranes (Sigma) was added to the wells after 3 washing steps. The reaction was stopped by intensive washing with UP water and the plates were allowed to dry overnight at 4° C. Images were taken using an immunospot reader (Luminoskan). Spots were counted manually based on size discrimination.

16. Competition Assays

Flow Cytometry

The flow cytometry-based competition assay is used to determine if the VHHs recognize similar epitopes on APN. The APN-transfected BHK-21 cell line was grown until reaching a 90% confluence and detached with StemPro accutase (Gibco). Detached cells ($3.0\times10^5$) were transferred to a conical bottom 96-well microtiter plate (Gibco) in 200 μl culture medium and centrifuged for 3 min at 350 g and 4° C. Next, BHK-APN cells were first incubated with 2L65, 3L2, 3L73 VHH-MG or a negative control at 40 ug/ml for 30 min on ice. Upon washing with PBS+1 mM EDTA, the cells were incubated with a second labeled 2L65, 3L2, 3L73 VHH-MG (AlexaFluor405 mouse IgG2a Zenon labeling kit) at 2 ug/ml for 30 min on ice. Upon washing with PBS+1 mM EDTA, cells were analysed with a flow cytometer (Cytoflex, Beckman Coulter). Dead cells were excluded using a propidium iodide staining. A total of 10,000 viable, single cells were measured for each condition (Cytoflex, Beckman Coulter).

Bio-Layer Interferometry

Epitope binning measurements are performed using biolayer interferometry at ambient temperature (BLI; Octet RED96). Here, 10 μg/ml biotinylated porcine APN (Sigma) in PBS is bound on a high precision streptavidin (SAX) biosensor soaked in PBS, followed by the addition of the VHHs at 500 nM in PBS+0.2% Tween-20+1% BSA (PBST+BSA). Next, 2L65 VHH is added at 250 nM in PBST+BSA. Data are analyzed with high-throughput epitope binning software.

ELISA 96-well ELISA plates (Nunc Polysorp®) are coated for two h at 37° C. with 400 ng of APN (Sigma) diluted in PBS. Plates are then washed three times with PBST and blocked overnight at 4° C. with 3% (w/v) gelatin prepared in PBS and 0.05% Tween-80. Following three washes with PBST, VHH-MG fusions are added to each well at a saturating concentration in dilution buffer (2% skimmed milk+PBS+0.05% Tween-20) and incubated for 1 h at RT. After washing, a biotinylated 2L65 VHH at 10 ug/ml in dilution buffer is added to each well and incubated for 1 h at RT. Bound biotinylated 2L65 VHH is detected by streptavidin-HRP (ThermoFisher scientific), diluted 1:5000 in dilution buffer. Following incubation for 1 h at RT, plates are washed three times with PBST and developed by adding HRP substrate (one SIGMAFAST™ OPD tablet dissolved in 20 ml deionized water). Finally, the reaction is stopped with 1 M hydrochloric acid and the optical density of the colorimetric reaction is measured at 492 nm (VersaMax™).

17. Statistical Analysis

The data were analyzed using GraphPad Prism 6. Serum antibody levels and the number of circulating antigen-specific antibody secreting cells were analyzed with two-way ANOVA and Dunnett's test for multiple comparisons. The number of intestinal antigen-specific antibody secreting cells were analyzed with a t-test and Holm-Sidak for multiple comparisons. The significance level was set at 0.05.

Results

1. Construction of an APN-Specific VHH Library

Figure 4:
FIG. 4: Screening of VHHs that bind APN-expressing cell lines. Crude periplasmic extracts were prepared from TG1 cells harboring recombinant phagemids from the library. The 28 APN-binding VHH candidates were screened on APN-expressing cell lines by flow cytometry. The clones were grouped according to their similarity in CDR3 sequence; numbers on top between the dotted lines refer to the family to which the different clones belong. The Y-axis represents the ratio of median fluorescence intensity (MFI) of APN-transfected (APN) and parental non-transfected BHK21 cells (parent).

To prepare an anti-APN VHH library, two llamas were immunized five times with commercially available kidney pAPN. A sixth booster was given with intestinal pAPN encoded by the same gene and prepared by the procedure as described in the Materials and Methods section. Two independent VHH-phage display libraries were constructed, each consisting of about $10^8$ transformants. After two consecutive rounds of panning, performed on stably transfected BHK21 cells expressing pig aminopeptidase N, 190 clones were randomly selected and sequenced. Through comparative alignment, VHHs having more than 80% percent sequence homology in their CDR3 region (B-cell lineages) were grouped as one family because they most likely recognize the same epitope (see ref. [26]) but their characteristics (e.g. affinity, expression yield, stability etc.) can be different. In this way, we obtained 28 unique VHHs belonging to 14 different families as candidate binders to APN (FIG. 4). These 28 unique VHHs were produced in *E. coli* cells and the crude periplasmic extracts were analyzed for their binding specificity via flow cytometry on pAPN-expressing BHK21 cells. The parental non-transfected BHK-21 cells served as negative control cells. An irrelevant VHH, (BCII10 specific for bacterial β-lactamase, described by Conrath et al. [27]) and a mouse anti-APN mAb IMM013 [4] were used as negative and positive control, respectively. This differential FACS analysis confirmed 22 of the originally 28 screened different VHHs belonging to 11 different families specific for porcine APN, demonstrating that the panning of the library on pAPN-transfected cells highly enriched for APN-binding VHH clones (FIG. 4).

2. Construction of a VHH-MG Expression Vector Via the BioXP DNA Printer

Because the FACS analysis for the panning on APN-transfected BHK-21 cells was performed with crude periplasmic extracts, the quality of binding of the different VHHs had to be further analyzed with purified proteins to allow comparison among the different VHHs and to rule out any experimental variables such as nanobody expression, periplasmic extraction efficiency, etc in the FACS analysis (FIG. 4). Important to realize is that some of the VHHs may contain an amber stop codon within the VHH sequence, because the VHH library with C-terminal histidine tag was prepared in the suppressor *E. coli* strain TG1 that reads the amber stop codon (TAG) as glutamine (Q). Thus, when an amber codon was identified by sequencing, it was also replaced by the glutamine codon.

Classically the selected VHHs are sub-cloned in direct fusion with an affinity tag in a non-suppressor *E. coli* strain, but here we followed a new strategy. We sub-cloned the VHHs in direct fusion with an Fc fragment to have the fusions produced in the medium of *Pichia pastoris*, providing the following advantages: Fc can be used as an affinity tag for protein purification, it makes the VHH-Fc fusion bivalent providing an avidity effect, and it allows comparison with the mouse monoclonal antibody IMM013 for APN binding as positive control. Twenty-eight selected VHHs were fused to the Fc domain of mouse IgG2a and cloned into an in-house *P. pastoris* expression vector. Two irrelevant VHHs, V2 [28] and D3 [29], specific for the F4 and F18 fimbriae of enterotoxigenic *E. coli*, respectively, were included as negative control.

Figure 1B:
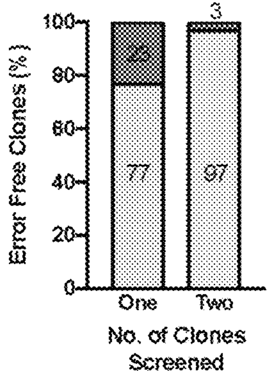

The sequences of the VHH and Fc domain were synthesized using the BioXP™ 3200 System and transformed into the yeast expression vector (FIG. 1*a*). All 30 constructs (with 28 selected VHHs and 2 negative controls) successfully built with the BioXP DNA printer were transformed into *E. coli* and four colonies per construct were analyzed by colony PCR or restriction digestion followed by sequencing to identify clones with the right insert. Twenty-three out of 30 constructs (77%) resulted in an error-free clone by sequencing only one colony, while for seven other VHH-MG constructs, two colonies had to be analyzed to obtain the right clone; for only one clone, i.e. 2L58MG (3%) the sequence was still incorrect in all four colonies, having one mutation in the coding sequence (FIG. 1*b*). Coincidently, this incorrect clone from family 12 was also negative in panning during VHH library preparation (FIG. 4). Therefore, we omitted it from the further analyses.

3. Yeast-Produced VHH-MG Fusions Bind Efficiently to Full-Length, Surface-Expressed APN The 29 obtained VHH-MG encoding constructs were then transformed into *Pichia pastoris*, and for each construct, four individual yeast colonies were screened to identify the transformant producing the highest amount of VHH-MG accumulating in the culture medium. Therefore, equal amounts of supernatant were analyzed by SDS-PAGE and by western blotting to examine the intensity of the recombinant protein signal and the integrity of the protein (FIG. 5). Only for the best expressing constructs, a band could be observed after SDS-PAGE; but for most constructs, a band was clearly present at the expected molecular weight after western blot analysis. The concentration of the different VHH-MGs produced in *P. pastoris* was determined using purified V2-MG and D3-MG reference proteins, and this ranged from 4 to 60 mg/l in 2 ml cultures, based on the analysis by ImageLab software. Only for some fusions, such as 3L11MG (family 10), 2L22MG (family 5) and V2-MG, a degradation product was detected besides the full-length product, suggesting that the VHH has an effect on the stability of the VHH-MG fusion as was also seen for VHH-IgA fusions [30].

Figures 2A, 2B:
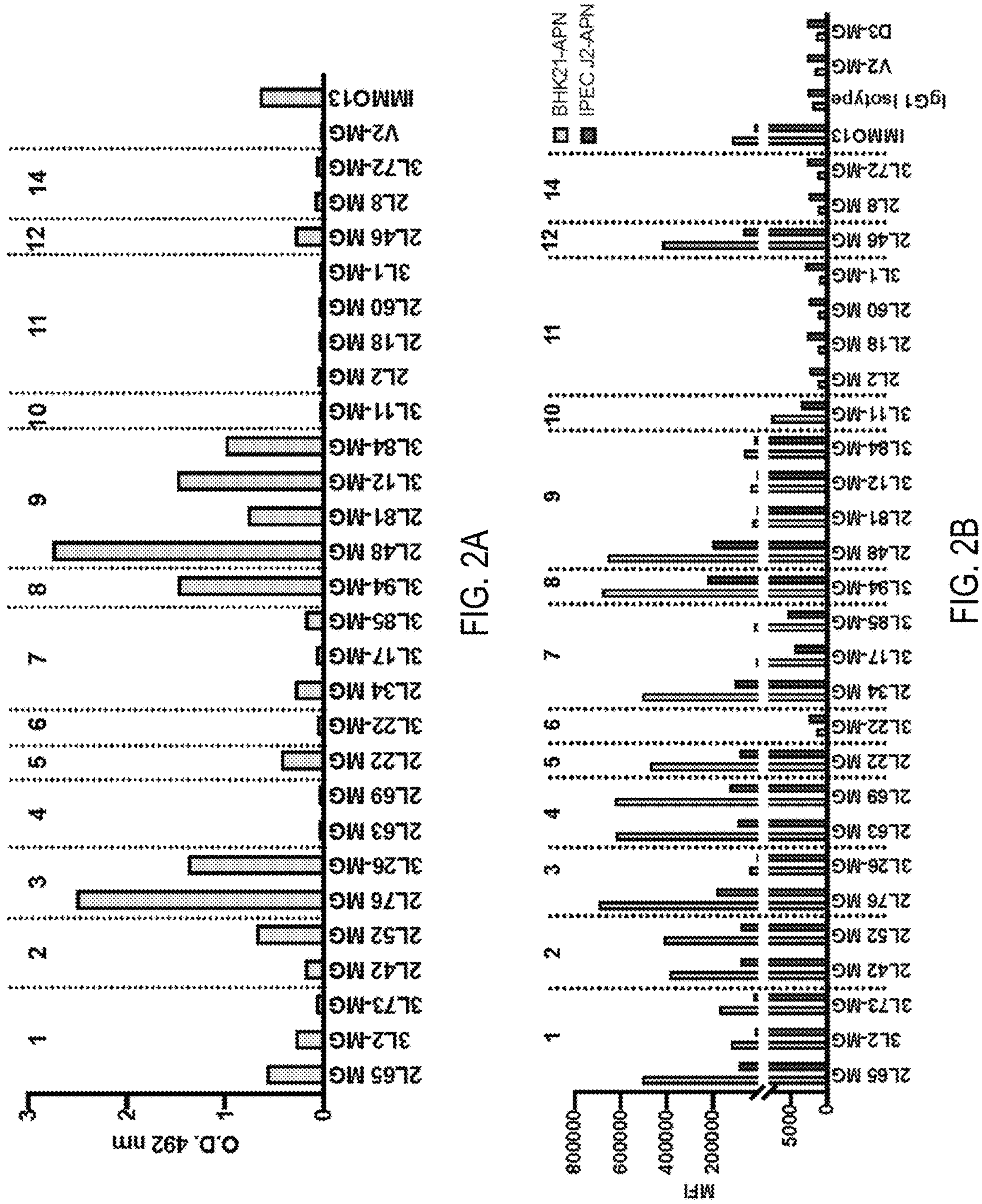
FIGS. 2A and 2B: Selection of APN-specific VHH-MG via ELISA and flow cytometry. Clones are arranged according to the family they belong to and separated by a dotted line.

Next, we determined the binding specificity of the VHH-MG fusions in a kidney APN-specific ELISA (FIG. 2*a*). Three-fold dilution series of VHH-MG in the culture supernatant were probed with anti-mouse IgG. The three strongest VHH-MGs, i.e. 2L48MG, 3L94MG and 2L76MG, displayed a strong binding activity to immobilized APN, each belonging to a different CDR3 group. These three VHH-MGs also showed good binding in the FACS assay performed after the panning to screen for phage displayed VHHs (FIG. 4). Interestingly however, some families of VHH-MG fusions were completely negative in the ELISA, for instance family 4 (2L63-MG, 2L69-MG), while they were strong binders in the FACS assay (FIG. 4). It is thus important to note that the relative binding activity on APN-coated wells in the ELISA assay did not correlate with the affinity of the VHH-MG fusions for the cell-expressed APN. Notably, VHH screening was performed via FACS using the cells expressing APN on their surface, so binding on immobilized APN might differ with binding on cells, perhaps because epitopes become less accessible during immobilization. Also, because the experiments were performed with crude medium samples, in which the VHH-MG protein accumulation was not equilibrated, the ELISA signal could be related to the protein concentration in the culture medium rather than to the affinity. (FIG. 2*a*, FIG. 4).

Figure 7:
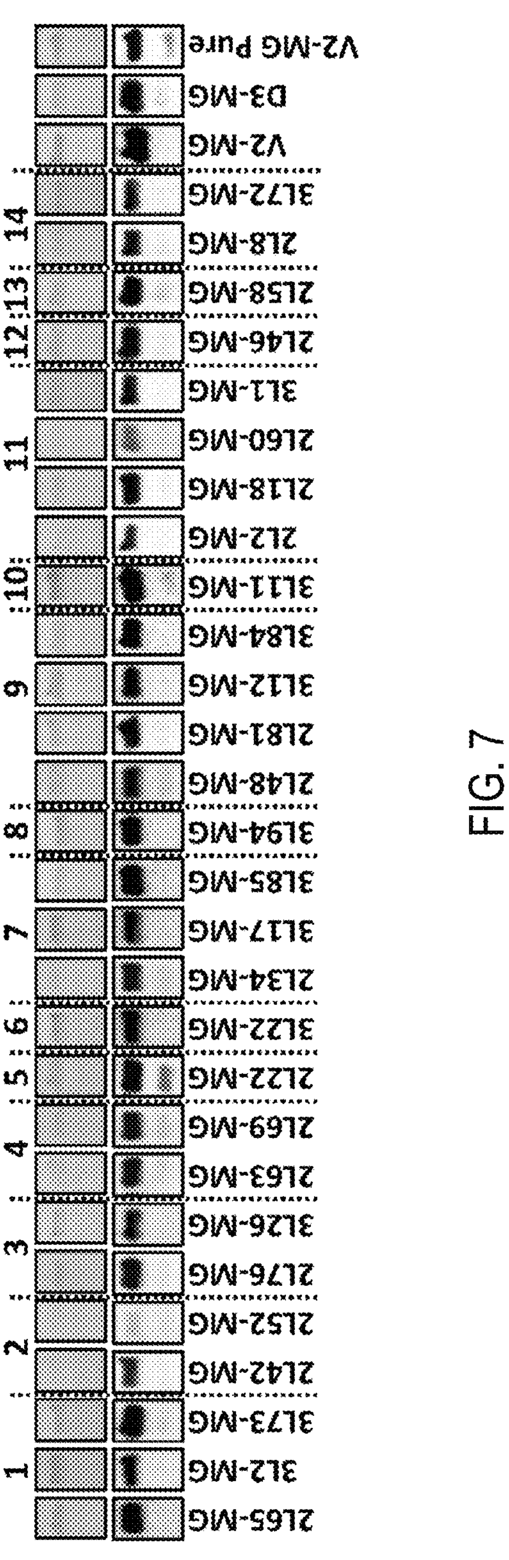
FIG. 7: Expression of different variants of APN-specific VHH-MG fusions in *Pichia pastoris*. The culture medium of yeast transformants (4 colonies for each construct) were screened by Coomassie staining and western blot analysis to identify the highest expressing clone. Here, only one high expressing clone for each construct is shown and they were grouped according to their CDR3 similarity; the numbers between the dotted lines represent the family to which they belong. Protein expression was induced for 48 h with 1% methanol. Cultures were harvested and supernatant was analyzed by SDS-PAGE (Top) and western blot (Bottom). 'V2-MG Pure' was used as a loading control and 500 ng of samples were loaded for Coomassie staining and 200 ng for western blot.

VHH-MG fusions were further assessed for their binding specificity and affinity on parent cell lines versus the derived transfected APN-expressing cell lines (BHK21 and IPEC-J2) via flow cytometry with equal amounts of VHH-MG protein (FIG. 2*b*). Of note, IPEC-J2 are porcine small intestinal epithelial cell lines which express low levels of APN on their surface and hence, only stably transfected cells were used. Based on the relative VHH-MG concentration, as determined by western blotting, equal molar amounts of the VHH-MG proteins and the positive control (IMM013) were spiked into spent medium of *P. pastoris*. Several strong APN-binders were identified based on the number of cells with bound VHH-MG through flow cytometry, whereas no binding was observed of spent medium with non-transfected BHK21/IPEC-J2 cells. Interestingly, family 4 (2L63 and 2L69), which was negative in an APN-specific ELISA, turned out to contain strong binders in the cell-based binding assay (FIG. 2*b*, FIG. 7). These findings were in line with the FACS data obtained from the crude periplasmic extract during VHH library screening (FIG. 4). We found that the amplitude of the binding activity on IPEC-J2-APN cells in comparison to BHK21-APN was significantly lower, which may be related to the amount of APN expressed on the IPEC-J2 cell membrane.

We selected at least one clone from the families showing binding activity in the flow cytometric screening (excluding family 6, 10, 11 and 14: families 6, 11 and 14 did not contain any APN binding VHHs; family 10 (3L11) displayed degradation and only low binding intensity) to further assess their affinity for small intestinal tissue via immunohistochemistry (IHC). Based on their binding activity, some clones were selected and purified for the in vivo analysis. Clones with low yield such as 2L76-MG, 2L34-MG and 2L52 were omitted from further analysis. Therefore, only six families containing strong (1, 4, 8, 9; about 100000 MFI) and moderate binders (5, 12; above 200000 MFI) are shown that were selected for upscaling. Each VHH-MG displayed binding to the intestinal ileum, whereas all controls were negative and did not show background; moreover, the intensity of the signal correlated with the binding activity in the FACS analysis (FIG. 2*b*).

Figure 3A:
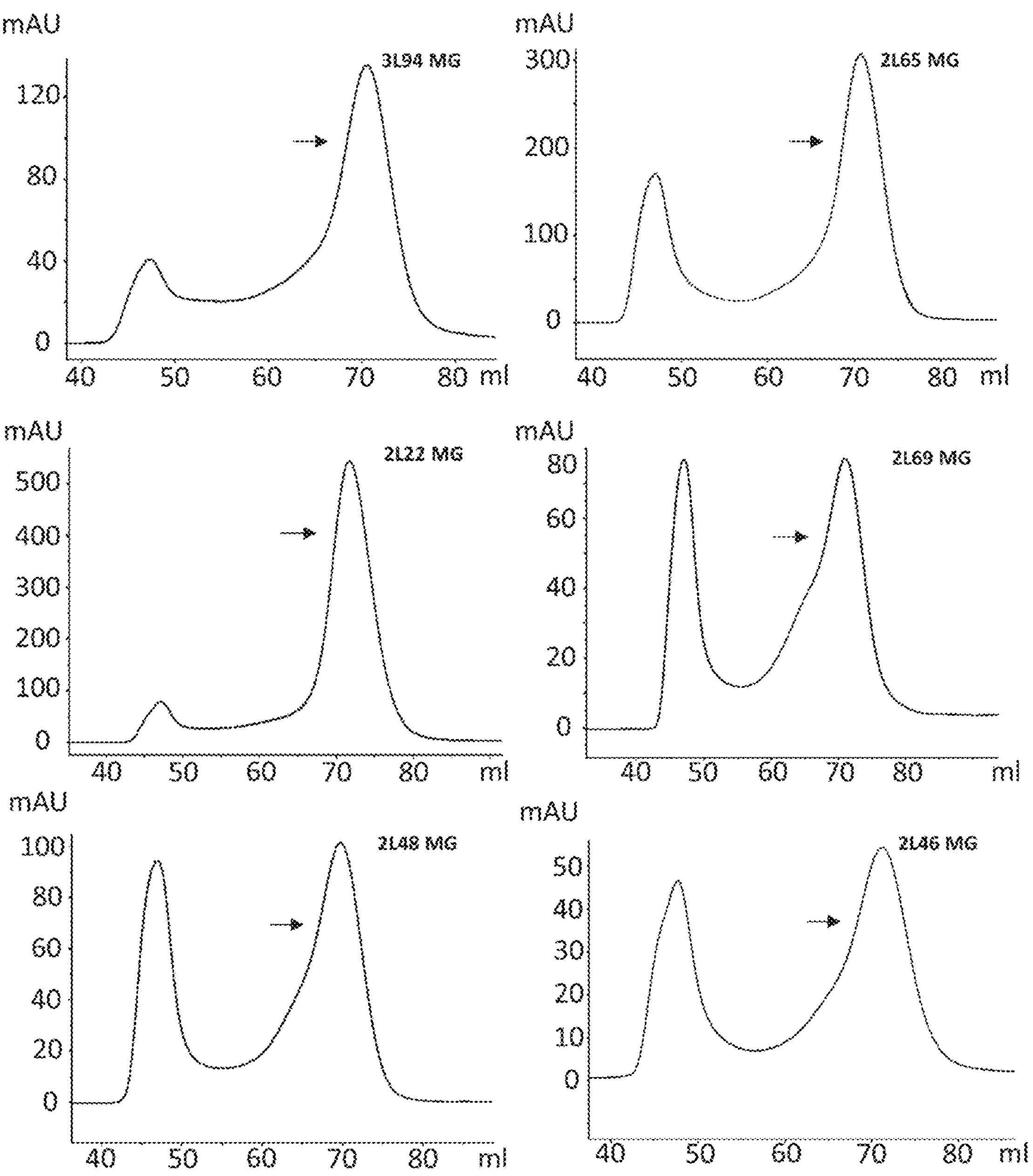
FIGS. 3A and 3B: Purification of the different VHH-MG fusions.

4. Purified APN-Binding VHH-MG Fusions are Internalized by Intestinal Epithelial Cells For each family, a single VHH-MG fusion displaying high expression and secretion in the spent *Pichia* medium and showing strong binding in FACS, was selected for upscaling. Secreted VHH-MG fusions were affinity purified on protein A and further assessed by size exclusion chromatography (SEC) (FIG. 3*a*). For most fusions, the SEC profile showed two major peaks, one representing aggregates and multimers, and one representing the monomer with the corresponding molecular weight of two associated VHH-MG polypeptides. The major portion of the 2L76 VHH-MG was found in aggregates; therefore, we excluded it from further analysis (data not shown).

Figure 3B:
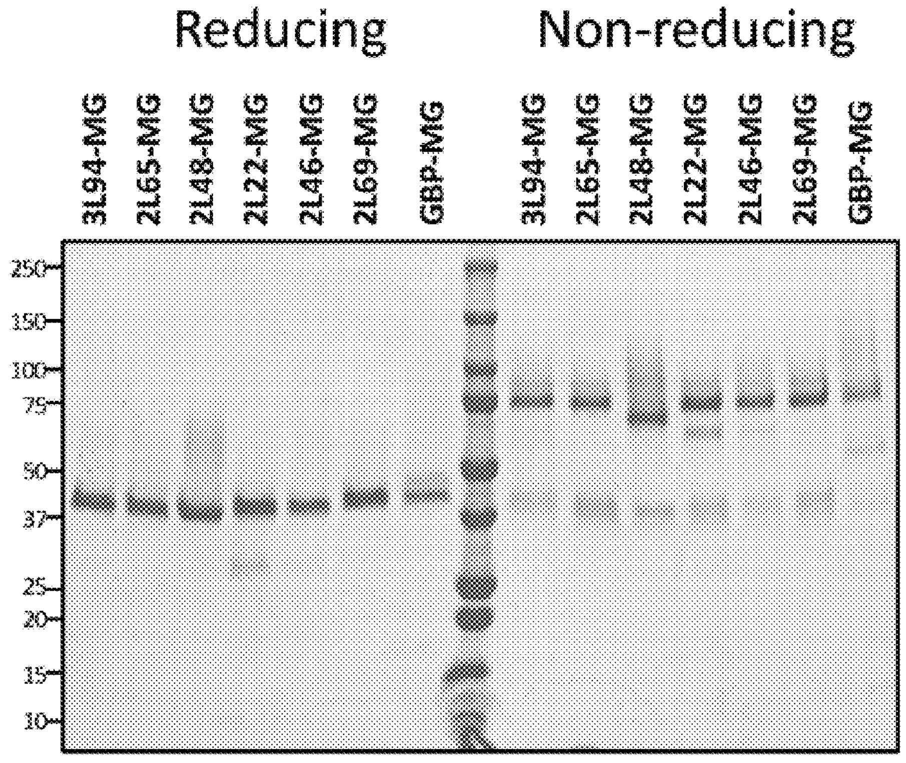

For the remaining six fusions, the fractions corresponding to the monomeric VHH-MG were pooled and further analyzed by SDS-PAGE under both reducing and non-reducing conditions to verify dimerization. Because peaks for monomers and aggregates in the SEC profile slightly overlap, the pooled purified VHH-MGs still contain a small quantity of aggregates. The samples on the non-reducing gel nicely displayed an 80 kDa band (FIG. 3*b*), which corresponds to a monomeric VHH-MG composed of two VHH-MG polypeptides of 40 kDa, as seen in the SDS-PAGE under reducing conditions. Moreover, some high-molecular weight bands that most likely represent the aggregates or glycan variants were also observed.

Figure 5A:
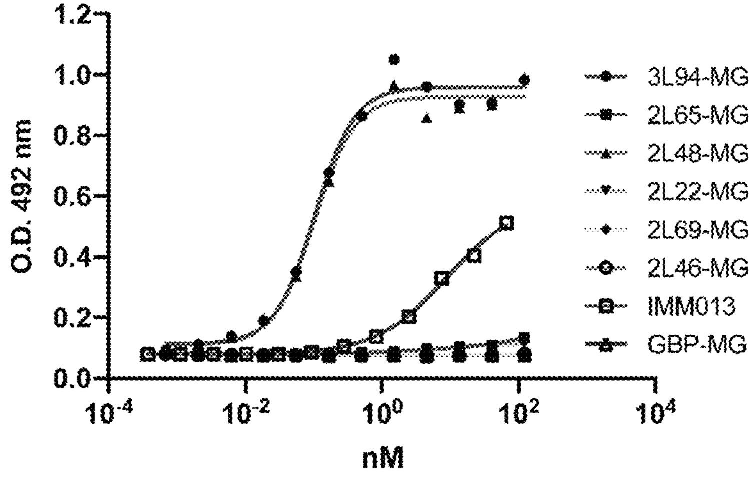
FIGS. 5A and 5B: Binding analysis and APN-mediated endocytosis of purified VHH-MG fusions.
Figure 5B:
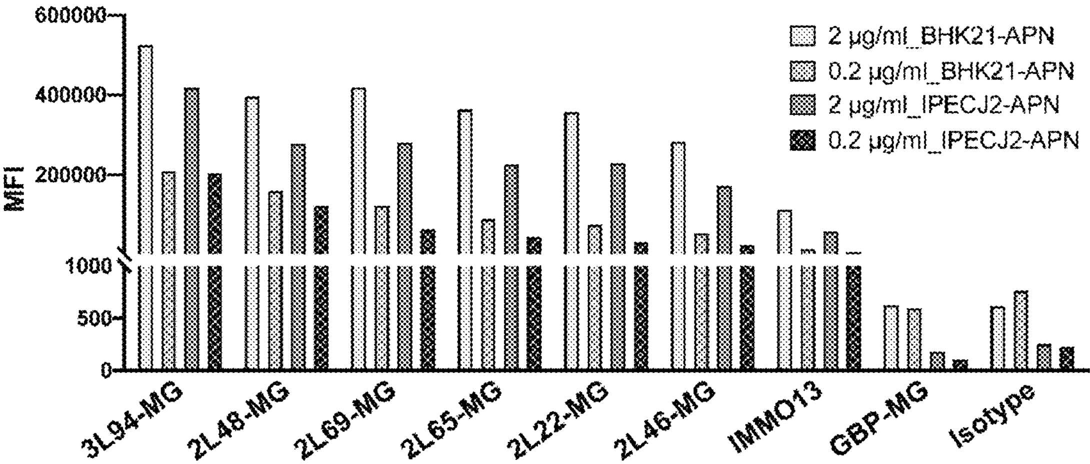

Next, we tested the binding characteristics of the different purified VHH-MG fusions in ELISA and FACS (FIGS. 5*a* and 5*b*, respectively). A GFP-specific VHH fused to a murine IgG3 (GBP-MG) was used as a negative control [23]. Although all of the six selected fusions showed strong binding on APN-expressing cells, the binding efficiency on the immobilized antigen in ELISA varied a lot, as was observed with the crude samples (FIG. 4).

Because efficient endocytosis by the target cell population of the potential vaccine-carrying system is of high importance to obtain a strong immune response, we further investigated whether the APN-binding VHH-MG fusions showed specific uptake by cells via the APN receptor. We used APN-expressing BHK21 cells because of their strong binding capacity of VHH-MG in FACS (FIG. 5*b*). The VHH-MG proteins were stained with a different fluorescent molecule to discriminate between membrane-associated VHH-MG and internalized VHH-MG via the APN receptor. Confocal imaging clearly demonstrated the APN-dependent uptake of VHH-MG fusions, because uptake of irrelevant VHH-MG fusions could not be observed. Three VHH-MG fusions (3L94-MG, 2L65-MG and 2L48-MG) were found to be the most potent APN binders and they displayed clear uptake signals only in APN-expressing cells.

Figure 11:
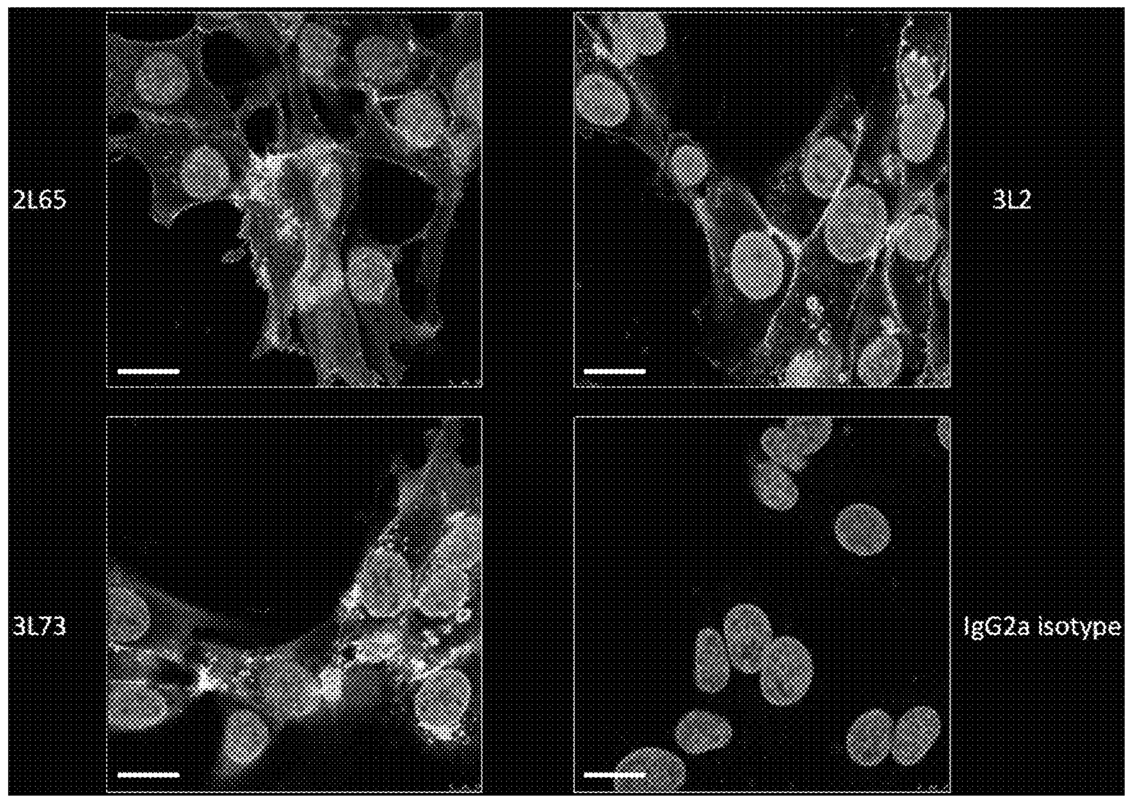
FIG. 11: APN-specific VHHs are internalised by BHK-APN cells.

It was furthermore confirmed by the endocytosis assay that 3L2 and 3L73 VHH trigger internalization similar to the 2L65 VHH, as shown in FIG. 11.

5. In Vivo Behavior of Selected APN-Specific VHH-Fc Candidates in a Gut Ligated Loop Assay To assess the in vivo behavior of the selected VHH-Fc IgG constructs, we performed a gut ligated loop assay in the small intestine (jejunum) of piglets. 3L94-MG and 2L65-MG were able to bind to the entire apical epithelium of the villi. In contrast, 2L48 and 2L22 showed a more patchy binding profile. It was seen that the binding profile is similar in different animals. In addition, 3L94-MG and 2L65-MG are endocytosed by the enterocytes in a similar way as IMM013. Based on this in vivo behavior in a gut ligated loop assay, we conclude that 3L94-MG and 2L65-MG are the most suitable candidates to target antigens to the small epithelium. Characterizing CDR1-3 regions of these single domain antibodies are given in table 3.

TABLE 3

| Clone | CDR1 | SEQ ID NO | CDR2 | SEQ ID NO | CDR3 | SEQ ID NO |
|---|---|---|---|---|---|---|
| 2L65 | GRTISNHAMG | 1 | AISWTGLTTN | 3 | RQSGYVSKFVDDYGY | 4 |
| 3L94 | GRTFSTYAMG | 14 | YISQLSLSTK | 15 | RSQNYVTTYDQSRAYDY | 16 |

Figure 6B:
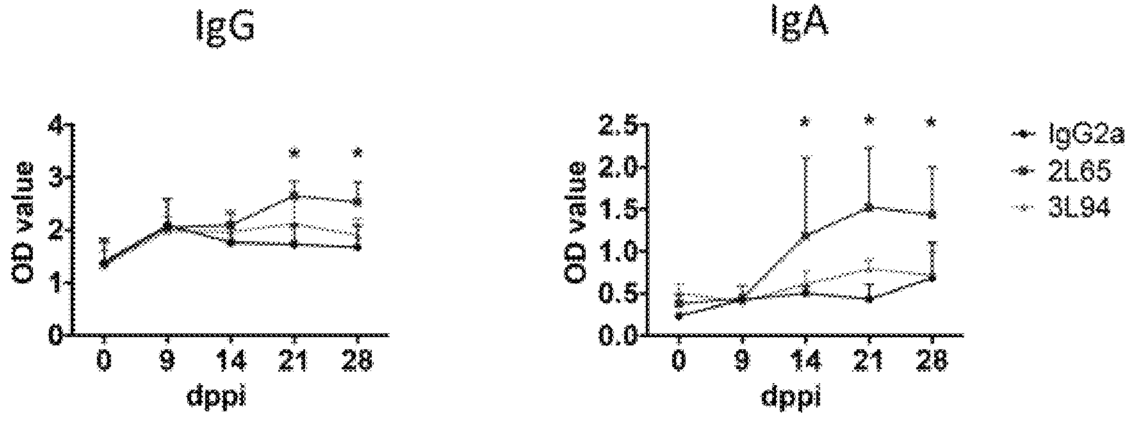
Figures 6C, 6D:
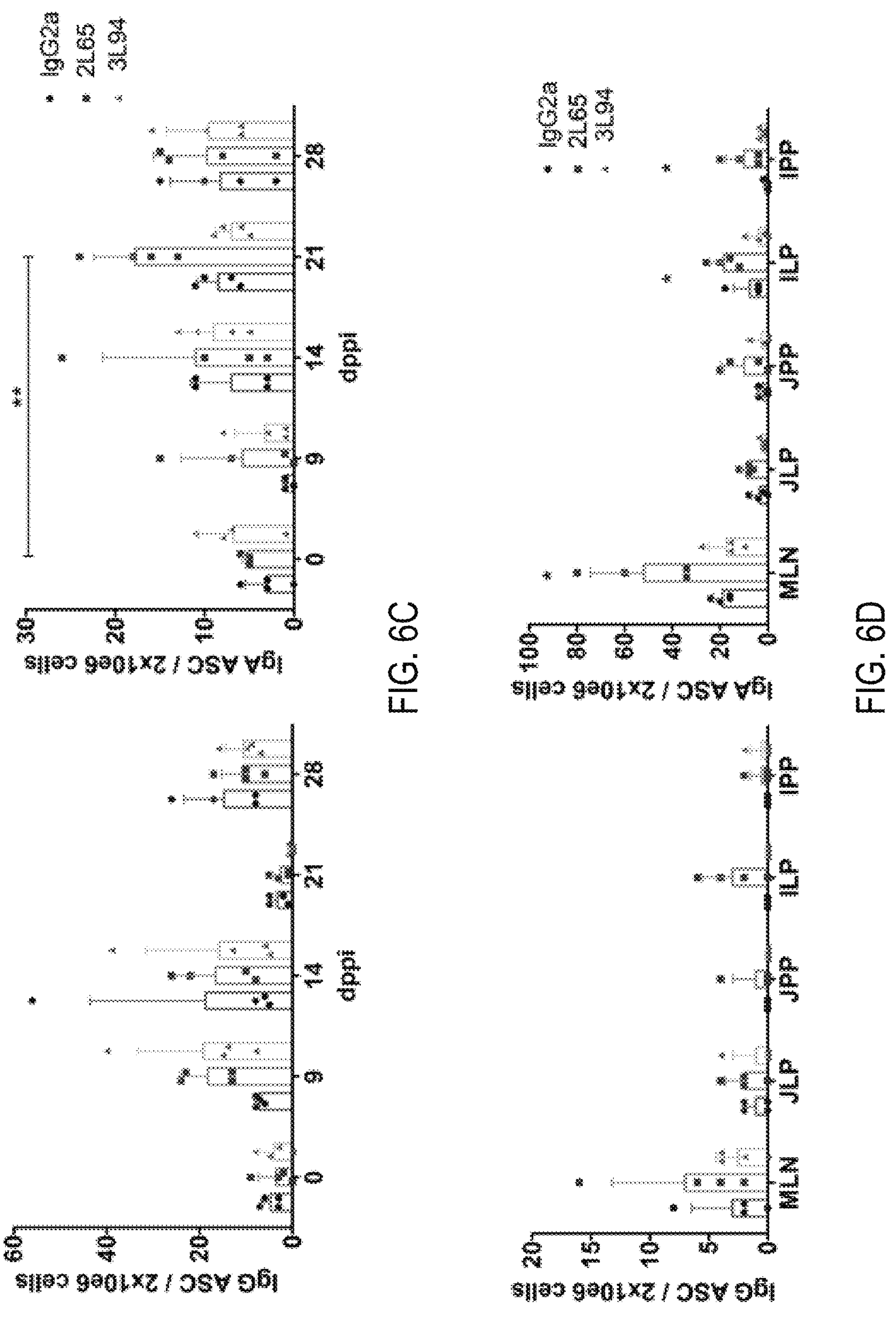

6. Oral Immunization with APN-Specific VHH-Fc Elicits Circulating and Small Intestinal Immune Responses To further demonstrate the potential of the selected VHH-MGs as vaccine delivery system, an oral immunization experiment in piglets was performed and the ensuing systemic and small intestinal immune responses were evaluated through detection of mouse Fc IgG2a-specific serum antibody responses and antibody secreting cells via ELISA and ELIspot, respectively. FIG. 6*b* shows that upon oral administration of 2L65-MG mouse Fc IgG2a-specific IgG and IgA serum levels were significantly increased as compared to the control group. Surprisingly, 3L94 did not promote mouse Fc IgG2a-specific serum antibody responses. In addition, oral immunization with 2L65-MG significantly increased the amount of circulating mouse Fc IgG2a-specific IgA secreting cells at 21 days post primary immunization as compared to day 0 and the control group (FIG. 6*c*). These results show that APN-specific VHH-MGs promote systemic immunity upon oral administration to piglets. To further show that also intestinal immune responses were enhanced, we evaluated the presence of mouse Fc IgG2a-specific antibody secreting cells in different small intestinal tissues via ELIspot. As shown in FIG. 6*d*, only 2L65-MG significantly enhanced the number of mouse Fc IgG2a-specific IgA secreting cells in mesenteric lymph nodes and ileal lamina propria and Peyer's patches at 28 dppi. Taken together, these results show that oral administration of 2L65-MG triggers systemic and small intestinal immune responses in piglets.

7. Competition Assay

This flow cytometry-based competition assay was used to determine if the VHHs recognize similar epitopes on APN. As shown in table 4, each VHH blocks the binding of the other VHH to the BHK-APN cells, indicating that these VHHs are competing VHHs binding very similar epitopes.

TABLE 4

Flow cytometry-based competition assay. The data are presented as median fluorescence intensity upon subtraction of the control values.

| | | second VHH (2 ug/ml) | | |
|---|---|---|---|---|
| | | 2L65 | 3L73 | 3L2 |
| first VHH (40 ug/ml) | / | 2878 | 4063 | 2277 |
| | 2L65 | 0 | 243 | 0 |
| | 3L73 | 0 | 0 | 0 |
| | 3L2 | 191 | 295 | 0 |

In conclusion, the present invention provides a family of VHHs having high sequence similarity (2L65, 3L2, 3L73) and not only binding APN expressing cells but also trigger transport through the small intestinal epithelium. Said family of VHHs moreover have the unique characteristic that they are able to induce systemic and intestinal IgA responses after oral administration, and in particular induce antigen-specific IgA+B cells.

REFERENCES

[1] V. Snoeck, W. Van den Broeck, V. De Colvenaer, F. Verdonck, B. Goddeeris, E. Cox, Transcytosis of F4 fimbriae by villous and dome epithelia in F4-receptor positive pigs supports importance of receptor dependent endocytosis in oral immunization strategies, Vet. Immunol. Immunopathol., 124 (2008) 29-40.

[2] B. Devriendt, B. G. De Geest, B. M. Goddeeris, E. Cox, Crossing the barrier: Targeting epithelial receptors for enhanced oral vaccine delivery, J. Control. Release, 160 (2012) 431-439.

[3] V. Melkebeek, K. Rasschaert, P. Bellot, K. Tilleman, H. Favoreel, D. Deforce, B. G. De Geest, B. M. Goddeeris, E. Cox, Targeting aminopeptidase N, a newly identified receptor for F4ac fimbriae, enhances the intestinal mucosal immune response, Mucosal Immunol., 5 (2012) 635-645.

[4] K. Baert, B. G. de Geest, R. de Rycke, A. B. da Fonseca Antunes, H. de Greve, E. Cox, B. Devriendt, β-glucan microparticles targeted to epithelial APN as oral antigen delivery system, J. Control. Release, 220 (2015) 149-159.

[5] B. Narasimhan, J. T. Goodman, J. E. Vela Ramirez, Rational design of targeted next-generation carriers for drug and vaccine delivery, Annu. Rev. Biomed. Eng., 18 (2016) 25-49.
[6] W. W. Cheng, T. M. Allen, The use of single chain Fv as targeting agents for immunoliposomes: an update on immunoliposomal drugs for cancer treatment, Expert Opin. Drug Deliv., 7 (2010) 461-478.
[7] C. R. Robinson, R. T. Sauer, Optimizing the stability of single-chain proteins by linker length and composition mutagenesis, Proc. Natl. Acad. Sci. USA, 95 (1998) 5929-5934.
[8] J. N. Duarte, J. J. Cragnolini, L. K. Swee, A. M. Bilate, J. Bader, J. R. Ingram, A. Rashidfarrokhi, T. Fang, A. Schiepers, L. Hanke, H. L. Ploegh, Generation of immunity against pathogens via single-domain antibody-antigen constructs, J. Immunol., 197 (2016) 4838-4847.
[9] T. De Meyer, S. Muyldermans, A. Depicker, Nanobody-based products as research and diagnostic tools, Trends Biotechnol., 32 (2014) 263-270.
[10] J. Helma, M. C. Cardoso, S. Muyldermans, H. Leonhardt, Nanobodies and recombinant binders in cell biology, J. Cell Biol., 209 (2015) 633-644.
[11] S. Muyldermans, Nanobodies: natural single-domain antibodies, Annu. Rev. Biochem., 82 (2013) 775-797.
[12] Ober et al. 2001, Intern. Immunology 13: 1551-1559.
[13] Drake et al. 2004, Analytical Biochemistry 328: 35-43.
[14] Fraley et al. 2013, Bioanalysis 5: 1765-74.
[15] Fontijn D et al., 2006, BRITISH JOURNAL OF CANCER, 94, 1627-1636).
[16] Imamura, Nobutaka, 2000. Leukemia and lymphoma, 37, 663-667.
[17] Xiao-Chi Jia et al. Journal of Immunological Methods 288: 91-98, 2004.
[18] Miller et al. Journal of Immunological Methods 365: 118-125, 2011.
[19] Davies and Riechmann, Prot. Eng. 9: 531-537, 1996.
[20] Kurtzman CP. Biotechnological strains of Komagataella (*Pichia*) *pastoris* are Komagataella phaffii as determined from multigene sequence analysis. J Ind Microbiol Biotechnol. 2009 November; 36(11):1435-8.
[21] C. Lundqvist, M.-L. Hammarström, L. Athlin, S. Hammarström, Isolation of functionally active intraepithelial lymphocytes and enterocytes from human small and large intestine, J. Immunol. Methods, 152 (1992) 253-263.
[22] E. Pardon, T. Laeremans, S. Triest, S. G. F. Rasmussen, A. Wohlkonig, A. Ruf, S. Muyldermans, W. G. J. Hol, B. K. Kobilka, J. Steyaert, A general protocol for the generation of Nanobodies for structural biology, Nat. Protoc., 9 (2014) 674-693.
[23] T. De Meyer, B. Laukens, J. Nolf, E. Van Lerberge, R. De Rycke, A. De Beuckelaer, S. De Buck, N. Callewaert, A. Depicker, Comparison of VHH-Fc antibody production in *Arabidopsis thaliana, Nicotiana benthamiana* and *Pichia pastoris*, Plant Biotechnol. J., 13 (2015) 938-947.
[24] A. Coddens, M. Loos, D. Vanrompay, J. P. Remon, E. Cox, Cranberry extract inhibits in vitro adhesion of F4 and F18+748 *Escherichia coli* to pig intestinal epithelium and reduces in vivo excretion of pigs orally challenged with F18+749 verotoxigenic *E. coli*, Vet. Microbiol., 202 (2017) 64-71.
[25] B. Devriendt, M. Gallois, F. Verdonck, Y. Wache, D. Bimczok, I. P. Oswald, B. M. Goddeeris, E. Cox, The food contaminant fumonisin B(1) reduces the maturation of porcine CD11R1(+) intestinal antigen presenting cells and antigen-specific immune responses, leading to a prolonged intestinal ETEC infection, Vet Res, 40 (2009) 40.
[26] E. De Genst, F. Handelberg, A. Van Meirhaeghe, S. Vynck, R. Loris, L. Wyns, S. Muyldermans, Chemical basis for the affinity maturation of a camel single domain antibody, J. Biol. Chem., 279 (2004) 53593-53601.
[27] K. E. Conrath, M. Lauwereys, M. Galleni, A. Matagne, J.-M. Frere, J. Kinne, L. Wyns, S. Muyldermans, β-Lactamase inhibitors derived from single-domain antibody fragments elicited in the Camelidae, Antimicrob. Agents Chemother., 45 (2001) 2807-2812.
[28] V. Virdi, A. Coddens, S. De Buck, S. Millet, B. M. Goddeeris, E. Cox, H. De Greve, A. Depicker, Orally fed seeds producing designer IgAs protect weaned piglets against enterotoxigenic *Escherichia coli* infection, Proc. Natl. Acad. Sci. USA, 110 (2013) 11809-11814.
[29] K. Moonens, M. De Kerpel, A. Coddens, E. Cox, E. Pardon, H. Remaut, H. De Greve, Nanobody mediated inhibition of attachment of F18 fimbriae expressing *Escherichia coli*, PLoS ONE, 9 (2014) e114691.
[30] S. Bakshi, A. Depicker, B. Schepens, X. Saelens, P. Juarez, A two-amino acid mutation in murine IgA enables downstream processing and purification on staphylococcal superantigen-like protein 7, J.768 Biotechnol., 294 (2019) 26-29.

The invention claimed is:

1. A polypeptide comprising at least one immunoglobulin single variable domain (ISVD), the ISVD comprising three complementarity determining regions (CDR), wherein:

(i) CDR1 is SEQ ID NO: 1, CDR2 is SEQ ID NO: 3, and CDR3 is SEQ ID NO: 4; or (ii) CDR1 is SEQ ID NO: 2, CDR2 is SEQ ID NO: 3, and CDR3 is SEQ ID NO: 5;

wherein the ISVD specifically binds CD13 and is internalized by CD13-expressing cells.

2. The polypeptide according to claim 1, wherein the polypeptide comprises a polypeptide having at least 80% sequence identity to SEQ ID NO: 6.

3. The polypeptide according to claim 1, wherein the polypeptide comprises an amino acid sequence selected from the group consisting of: SEQ ID NO: 6, SEQ ID NO: 7, and SEQ ID NO: 8.

4. The polypeptide according to claim 1, further comprising an Fc domain.

5. A chimeric molecule comprising the polypeptide according to claim 1, and a compound.

6. A nucleic acid encoding the polypeptide according to claim 1.

7. A host cell comprising the nucleic acid of claim 6.

8. A pharmaceutical composition comprising, in combination with a pharmaceutically acceptable carrier, excipient, and/or diluent:

(a) the polypeptide according to claim 1; or (b) a chimeric molecule comprising the polypeptide and a compound; or (c) a nucleic acid encoding the polypeptide; or (d) a host cell comprising a nucleic acid that encodes the polypeptide.

9. A method to produce the polypeptide according to claim 1, the method comprising:

introducing a nucleic acid encoding the polypeptide in a *Pichia pastoris* expression system, and purifying the expressed polypeptide.

10. The polypeptide according to claim 2, wherein the polypeptide comprises SEQ ID NO: 6.

11. The pharmaceutical composition according to claim 8, wherein the pharmaceutical composition is formulated for administration to a subject.

12. The pharmaceutical composition according to claim 11, wherein the pharmaceutical composition is formulated for oral, parenteral, topical, nasal, ophthalmic, intrathecal, intraventricular, sublingual, rectal, or vaginal administration.

13. The pharmaceutical composition according to claim 8, wherein the pharmaceutical composition is a vaccine.

14. The pharmaceutical composition according to claim 13, wherein the vaccine is a mucosal vaccine.

15. A method of treating an intestinal disease in a subject in need thereof, the method comprising administering to the subject an effective amount of the polypeptide according to claim 1.

16. The method according to claim 15, wherein the intestinal disease is a gut infection, an intestinal infection, a gut inflammation, or an intestinal inflammation.

* * * * *